US007947799B2

(12) United States Patent
Landskron et al.

(10) Patent No.: US 7,947,799 B2
(45) Date of Patent: May 24, 2011

(54) HIGH ORGANIC GROUP CONTENT-PERIODIC MESOPOROUS ORGANOSILICAS (HO-PMO'S)

(76) Inventors: Kai Manfred Martin Landskron, Toronto (CA); Benjamin David Hatton, Hamilton, CA (US); Geoffrey Alan Ozin, Toronto (CA); Doug Dragan Perovic, Toronto (CA)

( * ) Notice: Subject to any disclaimer, the term of this patent is extended or adjusted under 35 U.S.C. 154(b) by 1044 days.

(21) Appl. No.: 11/232,431

(22) Filed: Sep. 22, 2005

(65) Prior Publication Data

US 2007/0173401 A1 Jul. 26, 2007

Related U.S. Application Data

(60) Provisional application No. 60/611,702, filed on Sep. 22, 2004.

(51) Int. Cl.
*C08G 77/50* (2006.01)

(52) U.S. Cl. .............................. 528/35; 528/34; 521/63

(58) Field of Classification Search .................... 528/34, 528/35; 521/63
See application file for complete search history.

(56) References Cited

U.S. PATENT DOCUMENTS 2,590,937 A * 4/1952 Clark .............................. 528/34
3,465,018 A * 9/1969 Atwell .......................... 556/406
5,565,529 A * 10/1996 Babich et al. ................. 525/431
5,861,468 A * 1/1999 Harkness et al. ............... 528/19
7,071,540 B2 * 7/2006 Lyu et al. ...................... 257/642
7,108,922 B2 * 9/2006 Lyu et al. ...................... 428/447
7,381,659 B2 * 6/2008 Nguyen et al. ................ 438/778
7,427,570 B2 * 9/2008 Marsh .......................... 438/758

OTHER PUBLICATIONS

Landskron et al., "Periodic Mesoporous Organosilicates Containing Interconnected [Si(CH2)] Rings", Science, Oct. 10, 2003; 302:266-269.*

Recent developments in the sysnthesis and chemistry of periodic mesoporous organosilicas, Asefa et al, Elsevier Science B.V., 2002.

Ordered mesoporous molecular sieves sythesized by a liquid-crystal template mechanism, Kresge et al, Nature, vol. 359, pp. 710-712, Oct. 22, 1992.

* cited by examiner

*Primary Examiner* — Margaret G Moore
(74) *Attorney, Agent, or Firm* — Lynn C. Schumacher; Hill & Schumacher

(57) ABSTRACT

The present invention provides a new class of organic/inorganic hybrid materials having $[ER]_n$ rings interconnected by E' atoms. In an embodiment a class of materials called high organic group content periodic mesoporous organosilicas (HO-PMO's) with $[SiR]_3$ rings interconnected by O atoms is described. The measured dielectric, mechanical and thermal properties of the materials suggest that an increased organic content achieved by the $[SiR]_3$ rings of a high organic group content periodic mesoporous organosilica leads to superior materials properties potentially useful for a wide range of applications including microelectronics, separation, catalysis, sensing, optics or electronic printing.

20 Claims, 22 Drawing Sheets

EtO OEt
Si
$H_2C$ $CH_2$
EtO—Si Si—OEt
C
EtO $H_2$ OEt

CTAB
$H_2O/NH_3$ 3
meso
O
Si
$H_2C$ $CH_2$
O—Si Si—
C
$H_2$ O
∞

HIGH ORGANIC GROUP CONTENT-PERIODIC MESOPOROUS ORGANOSILICAS (HO-PMO'S)

CROSS REFERENCE TO RELATED U.S. APPLICATION

This patent application relates to, and claims the priority benefit from, U.S. Provisional Patent Application Ser. No. 60/611,702 filed on Sep. 22, 2004, which is incorporated herein by reference in its entirety.

FIELD OF THE INVENTION

The present invention relates to new hybrid organic-inorganic materials, denoted high organic group content periodic mesoporous organosilicas (HO-PMO's), which are built of interconnected cyclic $[SiR]_n$ ring building blocks with more than one organic bridging group tethered to each silicon atom.

BACKGROUND OF THE INVENTION

Materials fashioned into a structure with a periodic arrangement of mesopores, (e.g. MCM 41), represent a special class of compounds that have realized novel applications in catalysis, separation science, and chemical sensing, (see Kresge, C. T., Leonowicz, M., Vartuli, J. C., Beck, J. C. Ordered mesoporous molecular sieves synthesized by a liquid-crystal template mechanism. Nature 359, 710-712 (1992)). Such compounds consist of condensed $SiO_4$ building units linked via Si—O—Si bonds.

In contrast, periodic mesoporous organosilicas (PMO's) consist of $SiO_3R$ building blocks, whereby R is an organic group bridging the Si atoms in the form Si—R—Si. They have attracted attention because their bridging organic groups inside the channel walls of the pores provide them with distinct chemical and physical properties (see Asefa, T., Ozin, G. A., Grondey H., Kruk, M., Jaroniec, M. Recent developments in the synthesis and chemistry of periodic mesoporous organosilicas. Stud. Surf. Sci. Catal. 141, 1 (2002)).

The organic groups determine the desired properties of the material, as 'property carriers'. Accordingly, a higher number of organic groups inside the channel walls of a PMO would be highly desirable, because improved and novel materials properties can be expected and realized. This goal can be achieved by the use of cyclic $(SiR)_n$ units with organic groups R bound to Si through Si—C bonds as building blocks for periodic mesoporous organosilicas, which is the main part of the invention.

Mesoporous silica based films are interesting for applications as low dielectric constant (k) materials because porosity decreases the k values as air has a k value of 1.01 whereby dense silica has a k value of ca. 4.5. However the k values of meso-silica are very humidity sensitive. It has been shown that the incorporation of terminal organic groups like $CH_3$ bound to Si in meso-silica networks is beneficial for both further decreasing the k values and making it less moisture sensitive. However the mechanical stability is reduced thereby limiting the number of $CH_3$ groups that can be incorporated into meso-silica. Therefore it is very desirable to develop new silica based mesoporous films having a very high number of bridging organic groups.

SUMMARY OF THE INVENTION

The present invention discloses a novel class of inorganic-organic hybrid materials comprised of $[ER]_n$ rings interconnected by E' atoms. The use of the rings are very advantageous because they facilitate producing a material with a high-organic group content in the resulting organic-inorganic hybrid material.

Specifically, in one aspect of the invention there is provided a polymeric material comprised of $[ER]_n$ rings, wherein ER units within a ring are interconnected by E—R bonds and wherein the $[ER]_n$ rings are interconnected by inorganic atoms E' via E-E' bonds, in which E and E' are inorganic elements, R is an organic group, n is an integer >1. In another aspect of the invention there is provided a periodic porous material, comprising a plurality of interconnected building units each including an element E covalently bound to two or more organic groups which bridge the element E with additional elements E on two or more neighboring building units, the interconnected building units forming a material having periodic pores.

The element E may preferably be Si but may also be another element including, but not limited to Si, Ge, Sn, P, B, Ti, and Zr. The element E' may preferably be 0, but it may also be another element including, but not limited to N, S, P, B.

The materials may be produced in powder form, monolith form or films, and in all cases they may be produced to be porous or non-porous. One way of producing porous materials is by use of template materials following by template removal to leave well-defined pores behind.

The use of interconnected $[SiR]_n$ (n>1) rings as building units gives polymeric organic-inorganic hybrid materials with a high organic group content. In one non-limiting example this was demonstrated by ionic surfactant or block copolymer template directed self-assembly of the cyclic organosilane compound $[SiCH_2(OEt)_2]_3$ into a high organic group content periodic mesoporous organosilica. The high organic group content renders improved materials properties demonstrated for the dielectric and mechanical properties of interest for microelectronics applications. It was further discovered that $CH_2$ groups of the $[SiCH_2(OEt)_2]_3$ ring molecule can be converted into CHLi groups by lithiation using t-BuLi. Subsequent substitution of the CHLi groups by an electrophile X and self-assembly of the resulting molecule $[SiCH_2(OEt)_2]_2[SiCHX(OEt)_2]$ exemplifies that a large and diverse family of ring-substituted high organic group content periodic mesoporous organosilicas can be created. Moreover it was discovered that this reaction can also be used to link rings by an organic group when a bifunctional electrophile like 1,3-dibromopropane or 1,4 dibromo but-2-ene is used. The presented examples are $\{[(EtO)_2SiCH_2]_2[(EtO)_2SiCH]\}_2\{(CH_2)_3\}$ and are $\{[(EtO)_2SiCH_2]_2[(EtO)_2SiCH]\}_2\{(CH_2CHCHCH_2)_3\}$ in which two $(SiR)_3$ rings are linked by a propane-1,3diyl group and a but-2-ene-1,4 diyl group. They can be self-assembled into a PMO. The high organic group content periodic mesoporous organosilicas are synthesized in powder and film morphologies.

Accordingly, in one embodiment of the present invention, there is provided a periodic porous material comprised of $[SiR]_n$ rings, wherein SiR units within a ring are interconnected by Si—R bonds, each Si atom being bound to two or more organic groups which bridge said Si atoms, and wherein said $[SiR]_n$ rings are interconnected by oxygen atoms O via Si—O bonds, in which R is an organic group, n is an integer >1, said material having periodic pores, said pores have a diameter in a range from about 0.5 nm to about 1000 nm.

Dielectric constant (k) measurements of films with various organic content made from mixtures of $[SiCH_2(OEt)_2]_3$ and $Si(OMe)_4$ show that the k values decrease with the organic group content. The elastic modulus increases with the organic group content. The films have sufficient thermal and mechanical stability for microelectronics applications. In one embodiment, the materials according to the present invention exhibit a dielectric constant (k) less than 3, preferably, in a range from about 1.5 to about 2.2. Furthermore, the materials according to the present invention exhibit an elastic modulus lamer than 2 GPa and a hardness greater than 0.5 GPa.

BRIEF DESCRIPTION OF THE DRAWINGS

The method of producing high organic group content periodic mesoporous organosilicas will now be described in accordance with the present invention by way of example only, reference is made to the accompanying drawings, in which.

DETAILED DESCRIPTION OF THE INVENTION

Figure 1A:
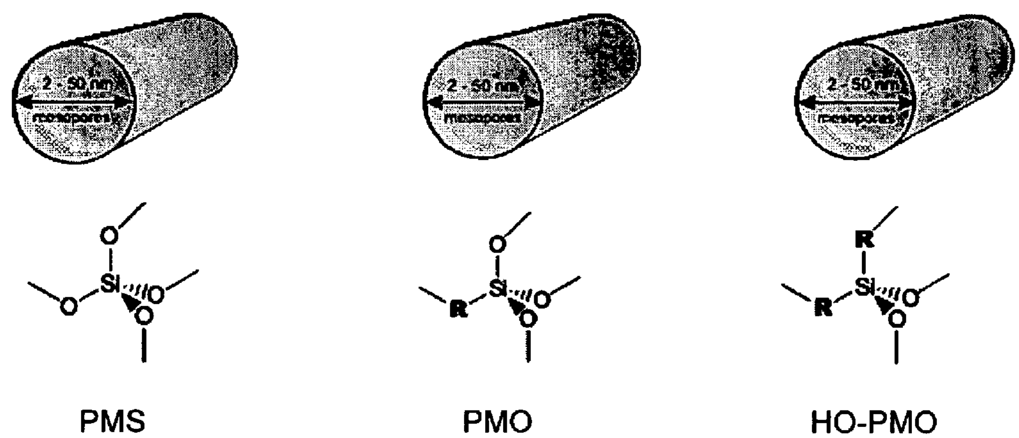
FIG. 1A compares the structures of Prior Art conventional periodic mesoporous organosilicas (PMOs), periodic mesoporous silicas (PMSs), and ring PMO's.

As used herein "organic group content" means the number of bridging organic groups bound to each element E.

As used herein "high organic group content" means a number of organic groups bound to each element E larger than 1.

As used herein, the term "high organic group content periodic mesoporous organosilica (HO-PMO)" means a periodic mesoporous organosilica with more than one organic bridging group tethered to each Si atom.

As used herein the term "inorganic element" E (or E') means any chemical element of the periodic table of the chemical elements except carbon C.

As used herein the term "organic bridging group" means an organic group, which is bound to at least two inorganic elements E atoms by E-C bonds.

As used herein "organic group" means a group of at least two atoms linked by chemical bonds, which contains at least one covalent carbon hydrogen bond.

As used herein the term "ring" means a molecule or a building unit of a molecule or a polymer containing one or more cycles of the type $[ER]_n$ (E=element, R=organic bridging group, n being an integer >1) with R bound to E by E-C bonds.

As used herein the term 3-ring means a ring of the type $[ER]_n$ with n=3.

As used herein, the term "template" means ionic and non-ionic molecules or polymers that have a structure-directing function for another molecule or polymer.

As used herein, the term "periodic mesoporous" means having an ordered arrangement of pores in terms of translation symmetry with a diameter between about 2 and about 50 nm.

As used herein the term "microporous" means having pores with a diameter <2 nm.

As used herein, the term "organosilica" means a organosilane compound that contains organic groups bound to two or more Si atoms.

As used herein, the term "self-hydrophobization" means a chemical reaction within a material that renders the material hydrophobic without the use of additional reagents.

In the present invention a novel class of periodic mesoporous materials comprised of cyclic $[ER]_n$ units as building blocks is disclosed. The synthesis of these materials is achieved by the template directed self-assembly of precursors with cyclic $[ER]_n$ units like $[Si(OEt)_2CH_2]_3$ into an periodic hybrid organic-inorganic mesoporous material consisting of $[ER]_n$ ring construction units that are interconnected by bridging atoms like O. We have exemplified this for HO-PMOs with E=Si, n=3 and various R. The template can be selected from single molecule, ionic or non-ionic surfactant assemblies, a block copolymer, or a colloidal crystal. The HO-PMO can be formed with any one of a number of mesostructures, exemplified by, but not limited to hexagonal structures, and various morphologies exemplified by, but not limited to powder and film morphologies.

HO-PMOs are structurally and compositionally distinct from all known periodic mesoporous silicas (PMSs)[1] and all known conventional periodic mesoporous organosilicas (PMOs)[2] because they have a highly organized, hierarchically-ordered pore wall structure comprised of inter-linked 3-ring cyclic building blocks with two bridging organic groups bound to each Si atom, a class of materials that was non-existent in the patent or open literature before the work described herein.

To emphasize this distinction, conventional PMOs have an organosilica framework comprised of acyclic bridging organic groups that straddle two Si atoms but with exclusively one bridging organic group bound to each Si atom whereas in sharp contrast the HO-PMOs have an organosilica framework comprised of cyclic bridging organic groups that straddle two Si atoms but with exclusively two bridging organic groups bound to each Si atom. These distinguishing structural and compositional features are illustrated in FIG. 1A. By using molecular cyclic organosilane compounds with $[SiR]_n$ rings as precursors, the organic group content of ring PMO materials can be significantly increased reaching an approximate composition of SiOR compared to $SiO_{1.5}R_{0.5}$ in conventional PMOs. Consequently the ring HO-PMOs described in this invention represent the first example of a new class of compounds that the inventors designate "high organic group content periodic mesoporous organosilicas (HO-PMO's)".

High organic group content periodic mesoporous organosilicas are defined as PMOs with more than one bridging organic group bound to each Si atom in the organosilica framework comprising the material. Furthermore, all known PMSs and PMOs that pre-date the HO-PMOs of this invention consist of simple inter-connected tetrahedral $SiO_4$ or $SiO_3R$ building units rather than the $SiO_2R_2$ units of the HO-PMOs described here. Because the bridging organic groups provide the PMO with some defined property, then consequently a higher number of organic groups bound to each Si atom in the framework of the material is expected to lead to distinct and superior materials properties and a wider range of novel applications. This was demonstrated for but not limited in any way by the dielectric properties of the HO-PMOs.

The present invention describes new materials, referred to as high organic group content periodic mesoporous organosilicas (HO-PMOs) with more than one bridging organic group bound to each Si atom. It is based on $[SiR]_n$ rings interconnected by O atoms fashioned into a structure with a periodic arrangement of mesopores. The HO-PMOs represent the first examples of materials with a polymeric network in which ring units of the type $[ER]_n$ (E=inorganic element) having E-C bonds are interconnected by atoms E' (E'=any element of the periodic table) via E-E' bonds.

Figure 1B:
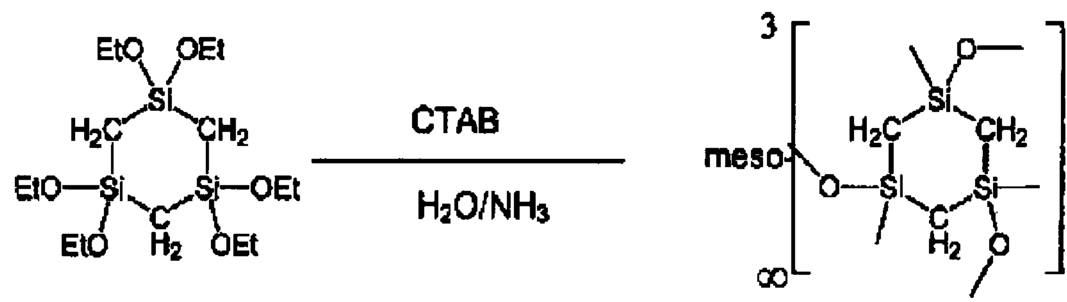
FIG. 1B shows a scheme for the self-assembly of 1. CTAB=cetyltrimethylammoniumbromide, the periodic mesoporous organosilica is illustrated on the right side of the figure and its channel walls consist of a three-dimensional polymeric organosilica network symbolized by a modified Machatschki symbol of the cyclic repeating unit (in brackets)

We have produced the first non-limiting examples of a high organic group content periodic mesoporous organosilicas. The synthesis (1) and self-assembly of the 1,3,5-tris[diethoxysila]cyclohexane $[(EtO)_2SiCH_2]_3$ cyclic organosilane precursor with a surfactant mesophase to create a PMO, in powder and film morphologies is illustrated in FIG. 1B. The preparation of the powder form utilizes the $NH_4OH$ base-catalyzed aqueous phase co-assembly of cationic cetyltrimethylammonium surfactant micelles with $[(EtO)_2SiCH_2]_3$. The surfactant can be extracted by several means, such as stirring in a methanol-HCl solution or calcination at 300° C. in a $N_2$ atmosphere.

We have furthermore demonstrated that the n organic groups R in the $[ER]_n$ ring can be either all identical (R), all different from each other (R1, R2, R3 . . . ), or some of them may be identical and the remaining ones different.

The materials may be produced with $[ER]_n$ rings with n equal to the same integer. However, it will be appreciated that materials may be made up of a mixture of $[ER]_n$ rings with non-identical n values can be prepared when mixtures of respective molecular precursors are polycondensed. For example the polymeric material may be made using a mixture of rings with n=2, 3 etc.

It will be furthermore appreciated that the material may also include additional terminal organic groups bound to the ring or when a cyclic precursor is mixed with a organosilane having terminal organic groups e.g. $CH_3Si(OMe)_3$, and then polycondensed.

It will be furthermore appreciated that the material may also include acyclic units comprising $EE'_4$, for example $SiO_4$ or $EE'_3REE'$, for example $O_3SiRSiO_3$, wherein the $[ER]_n$ rings and the acyclic units are interconnected by the E' atoms. This can be accomplished by copolycondensation of the cyclic precursor with an acyclic precursor.

We furthermore demonstrate in the examples 5 and 6 discussed hereinafter that the material can also be comprised of building blocks of a discrete number of $[ER]_n$ rings that are interconnected by an organic group linking the organic groups of the $[ER]_n$ rings.

It will be appreciated that porous examples of the materials may be made by polycondensing cyclic molecules containing said $[ER]_n$ rings in the presence of a template material under conditions suitable for self-assembly of the cyclic molecule and removing the template material from the self-assembled cyclic molecule.

The template material may be a tetraalkyl ammonium salt, or a blockcopolymer can be used. Other template materials that can be used include, but are not restricted to, non-ionic and ionic templates like star-shaped molecules, other macromolecules, dendrimers or colloidal crystals.

The details about the invention regarding synthesis, characterization and properties of high organic group content periodic mesoporous organosilicas will now be described. The material is produced by polycondensing a cyclic molecule containing the $[ER]_n$ rings under conditions suitable for polycondensation of the cyclic molecule. The following non-limiting examples of cyclic organosilanes $[SiCH_2(OEt)_2]_3$ (1), $[SiCH_2(OEt)_2]_2[SiCHX(OEt)_2]$ (X=Br, I, Et) (2, 3, 4), $\{[(EtO)_2SiCH_2]_2[(EtO)_2SiCH]\}_2\{(CH_2)_3\}$ (5) and $\{[(EtO)_2SiCH_2]_2[(EtO)_2SiCH]\}_2\{CH_2CHCHCH_2\}$ (6) are used as precursors for high organic group content periodic mesoporous organosilicas.

Example 1

Synthesis of a HO-PMO as a Powder with the Approximate Composition $SiOCH_2$ The synthesis of $[SiCH_2(OEt)_2]_3$ was performed according to literature as disclosed in D. J. Brondani, R. J. P. Corriu, S. El Ayoubi, J. E. Moreau, M. W. C. Man, *Tetrahedron Letters* 34, 2111 (1993).

Synthesis of a high organic group content periodic mesoporous organosilica with an approximate composition of $SiOCH_2$ was as follows. Cetyltrimethylammoniumbromide (0.9 mmol, 0.32 g, Aldrich) was dissolved in a mixture of 2.16 g $NH_4OH$ (35 wt %) and 3.96 g de-ionized water at 20° C. $[(EtO)_2SiCH_2]_3$ (1.26 mmol, 0.5 g) were added to this solution, which was stirred for 24 h at 20° C. while a white precipitate formed. Afterwards the mixture was aged for 24 h at 80° C. The precipitate was filtered off and washed with copious amounts of water. The as-synthesized sample was then stirred for 48 h in a solution of 12 g HCl (36 wt %) and 80 g of methanol. The sample was then filtered off again and washed with copious amounts of MeOH, to yield the surfactant extracted HO-PMO as a powder.

Characterization of the High Organic Group Content Periodic Mesoporous Organosilica of Example 1

Figure 2A:
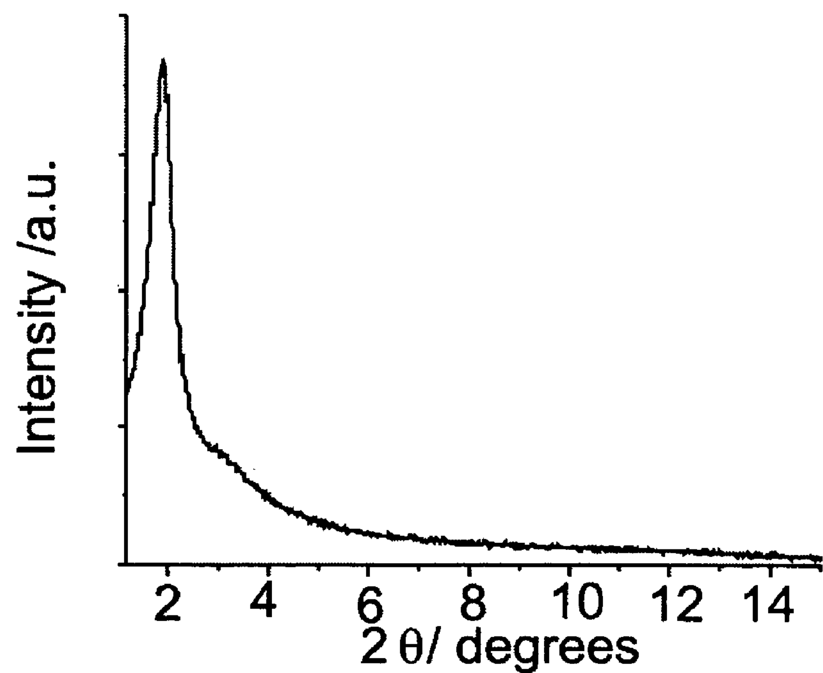
FIG. 2A shows a powder x-ray diffraction pattern of the powder form of the surfactant-extracted PMO composed of $[SiCH_2]_3$ rings.
Figure 2B:
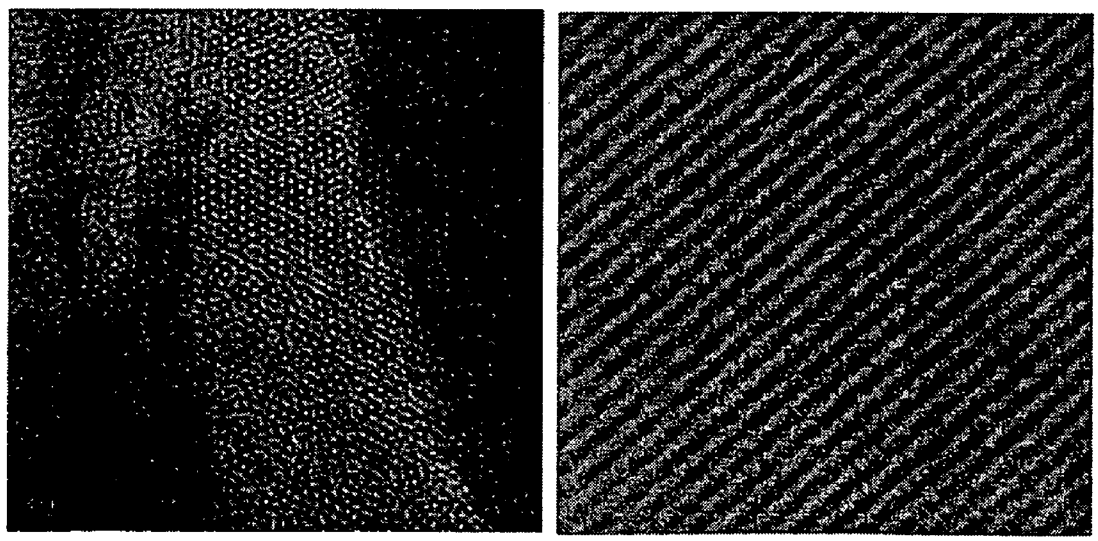
FIG. 2B shows TEM images of the powder form of the surfactant-extracted PMO referred to in FIG. 2A.

FIG. 2A shows the powder x-ray pattern of the surfactant-extracted PMO obtained from 1. The 100 reflection gives a d-spacing of ~4.7 nm. Transmission electron microscopy TEM images of the PMO provided additional structural information, showing the presence of periodic arrays of parallel aligned mesoscale channels with a spacing of ~4.5 nm, mesopores with a diameter of ~2.2 nm and an estimated channel wall thickness of 2.3 nm (FIG. 2B). $^{29}$Si-MAS-NMR spectroscopy of the PMO showed that no significant Si—C bond cleavage occurred during the synthesis.

Figure 2C:
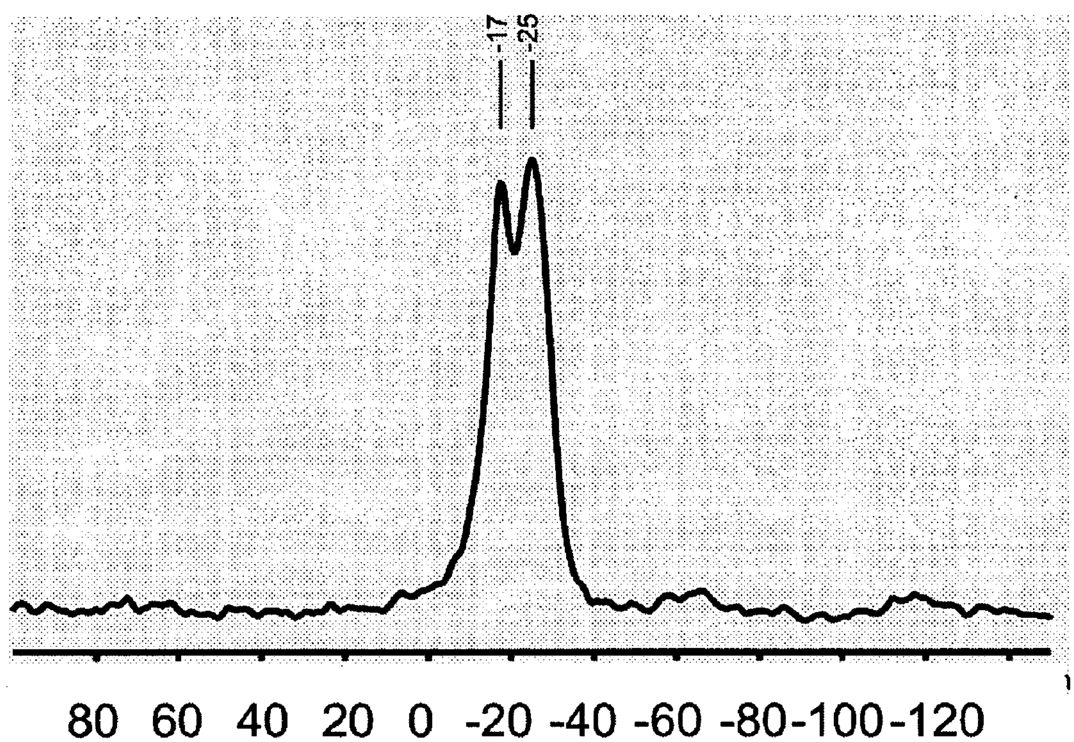
FIG. 2C shows a $^{29}$Si MAS NMR spectrum of the surfactant-extracted PMO of FIGS. 2A and 2B.
Figure 2D:
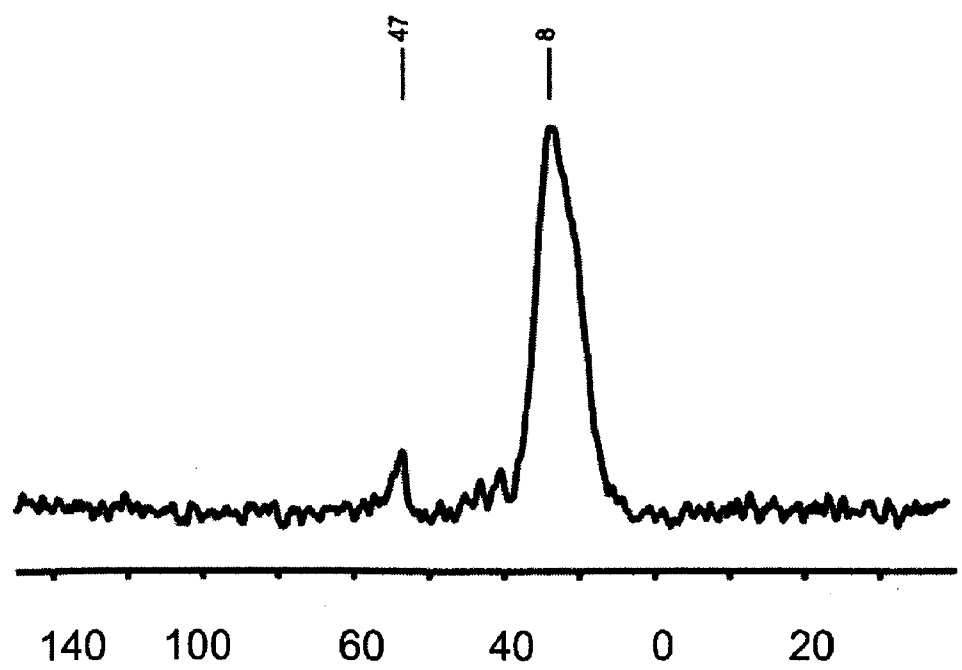
FIG. 2D shows $^{13}$C CP MAS NMR spectrum of the surfactant-extracted PMO composed of $[SiCH_2]_3$ rings.

To expand on this key point, the surfactant-extracted material (FIG. 2C) shows two peaks at −17 and −25 ppm, which can be assigned to $D_1$ $(CH_2)_2Si(OSi)(OH)$ and $D_2$ $(CH_2)_2Si(OSi)_2$ tetrahedral building units. [2-3] $^{13}$C-MAS-NMR spectroscopy of the PMO indicates that full removal of the surfactant had occurred by showing a peak at 8 ppm typical for $CH_2$ groups tethered to two Si atoms and a small signal at 47 ppm indicating some methoxylation of silanol groups during surfactant extraction (FIG. 2D). By comparison all PMOs synthesized to date[4-6] only show $T_{1,2,3}$ $RSi(OSi)_{3-x}(OH)_x$ tetrahedral sites in their $^{29}$Si-MAS-NMR spectra diagnostic of interconnected tetrahedral $SiO_3R$ building blocks.

Elemental analysis of the fully extracted PMO revealed 43% Si, 21% C, 29% 0 and 4.1% H content, which is close to the theoretical values for $SiOCH_2$ (48.2% Si, 20.6% C, 27.6% O, 3.4% H). Also, it should be noted the correct stoichiometry is $SiO_{1-x}(OH)_{2x}CH_2$ due to additional silanol groups.

Thermogravimetry analysis (TGA) of the surfactant-extracted PMO performed in nitrogen revealed no significant mass loss up to 500° C. except physisorbed water between 20 and 100° C.

Figure 3A:
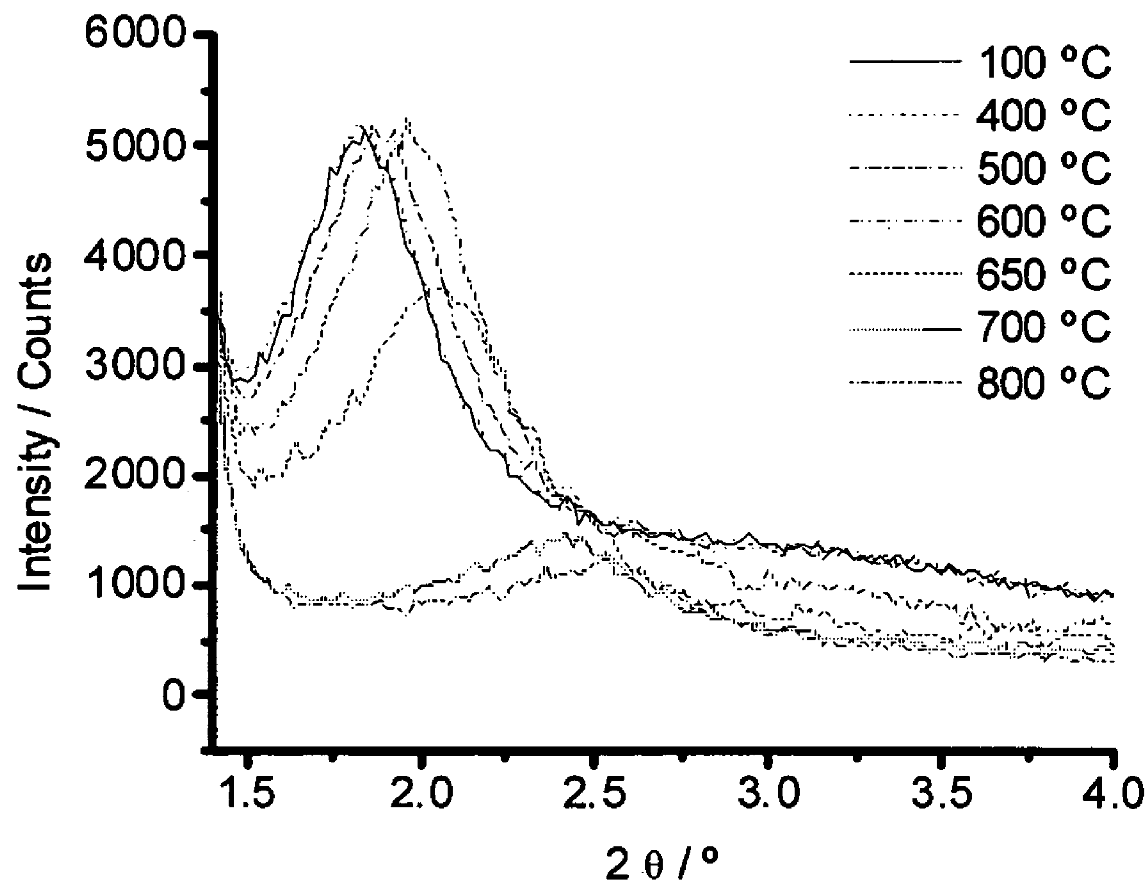
FIG. 3A shows temperature dependent studies of the powder x-ray diffraction (PXRD) of the synthesized PMO composed of $[SiCH_2]_3$ rings performed under $N_2$ in which the mesopores remain intact up to 600° C. without loss of order and no pore-shrinkage occurs up to 500° C.
Figure 3B:
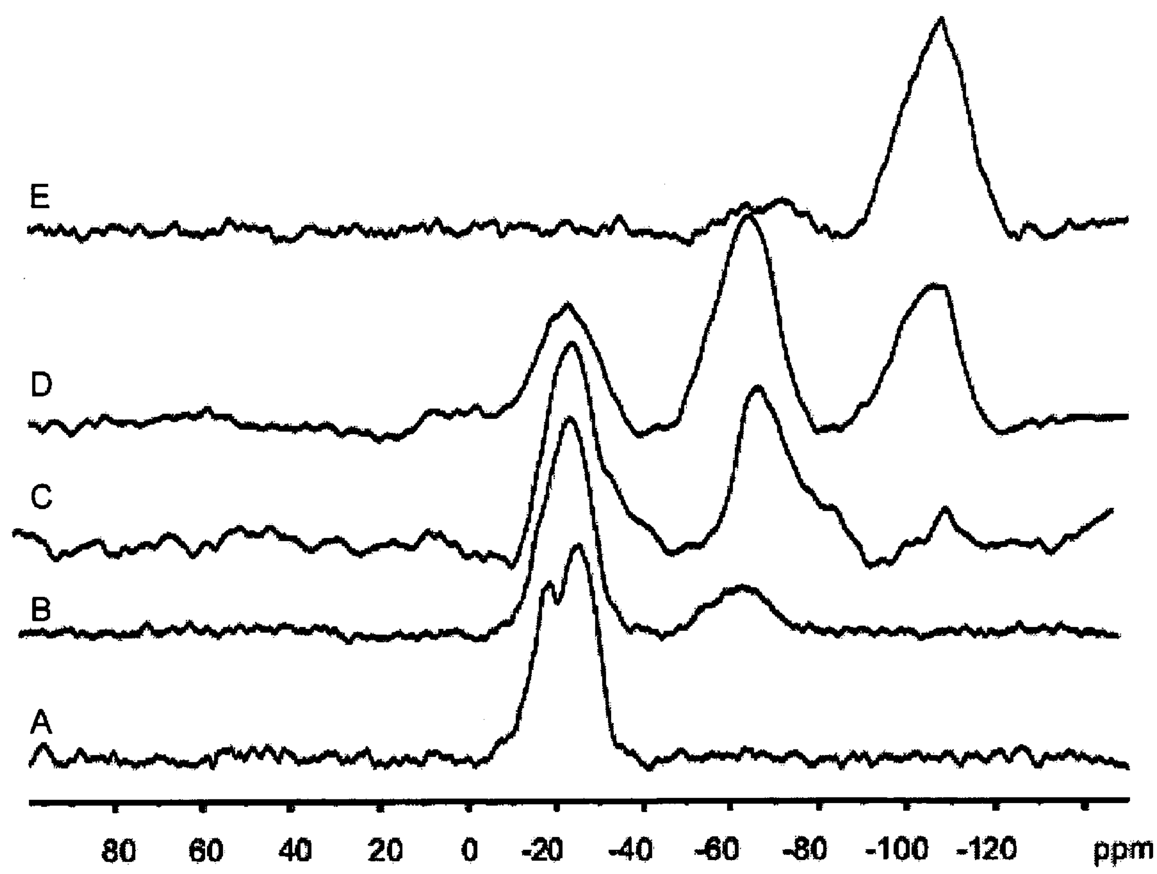
FIG. 3B shows temperature dependent studies of the $^{29}$Si MAS NMR spectra of the powder form of surfactant-extracted PMO composed of $[SiCH_2]_3$ rings treated thermally over the temperature range 300° C. (A), 400° C. (B), 500° C. (C), 600° C. (D) to 700° C. (E) in $N_2$ atmosphere.

The order of the mesoporosity of the PMO remains intact up to 600° C. with no pore shrinkage up to 400° C., as shown by temperature dependent PXRD under $N_2$ (FIG. 3A). $^{29}$Si MAS NMR spectroscopy of thermally treated samples under $N_2$ (FIG. 3B), showed only signals for $D_1$ $(CH_2)_2Si(OSi)(OH)$ and $D_2$ $(CH_2)_2Si(OSi)_2$ sites up to 300° C. Above 400° C., silanol-facilitated transformation of the $CH_2$ groups into terminal $CH_3$ groups occurs, which are eliminated above 500° C., as $^{29}$Si MAS NMR (FIG. 3B), and $^{13}$C NQS MAS-NMR experiments have shown.

Figure 5:
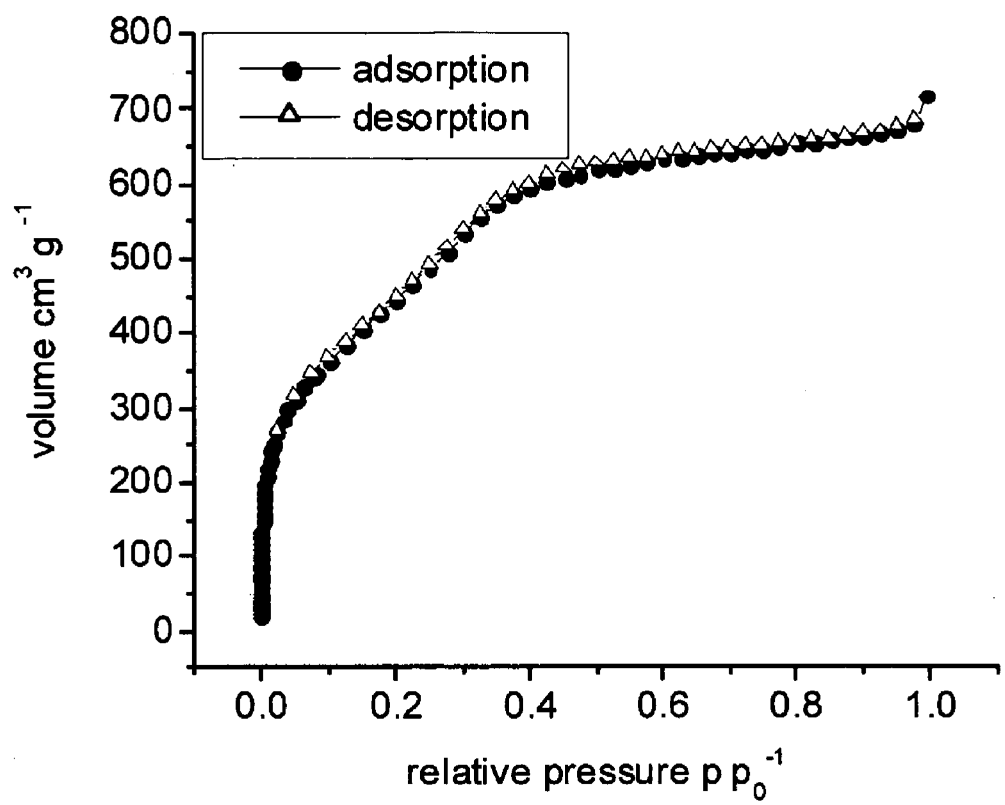
FIG. 5 shows nitrogen adsorption data for the powder form of the surfactant-extracted PMO composed of $[SiCH_2]_3$ rings, the diagram shows the type IV $N_2$ isotherm with the BJH analysis of the mesopores (inset)

Analogous silanol-facilitated methene bridge to terminal methyl, and finally to methyl group loss sequence of thermal transformations have been observed in the periodic mesoporous methenesilica (meso-$SiO_{1.5}(CH_2)_{0.5}$) synthesized from the organosilane precursor bis(triethoxysilyl)methane $(Eto)_3SiCH_2Si(OEt)_3$.[7] Nitrogen adsorption data for the powder form of the PMO shows a diagnostic type IV isotherm with well-defined capillary condensation and very little hysteresis (FIG. 5).

The Brunauer Emmett Teller BET surface area is found to be as high as 1706 $m^2/g$ and the mesopore diameter is about 2.5 nm, calculated by BJH methods (FIG. 5) consistent with TEM measurements (FIG. 2B). This adsorption data, together with the d-spacing of 4.7 nm given by PXRD, provides an independent estimate of the channel wall thickness of about 2.2 nm thereby corroborating the TEM measurements of the diameter of the mesopores and thickness of the channel walls. Density functional theory (DFT) analysis of the low pressure arm also suggests the presence of micropores with diameters in the range of 1.0-1.5 nm.

Example 2

Synthesis of a HO-PMO as a Film with the Approximate Composition $SiOCH_2$

Films were made by spin-coating a synthesis solution at rates of 1200 to 3600 rpm onto glass or a Si (100) wafer. A typical synthesis would involve mixing 0.356 g of $10^{-3}$M HCl, 0.568 g EtOH, and 0.450 g aqueous cetyltrimethylammonium chloride solution (25 wt. %, Aldrich) to make a homogeneous solution, then adding 0.488 g of $[(EtO)_2SiCH_2]_3$ (molar ratio 1.0:31.3:2.89×$10^{-4}$:10:0.285 of $[(EtO)_2SiCH_2]_3$:$H_2O$:HCl:EtOH:cetyltrimethylammonium chloride). After spin-coating the films were dried in air at room temperature for 24 h and washed in DI $H_2O$ before calcination at 300° C.-500° C. under flowing nitrogen for 5 h, using a heating rate of 1° C./min. The films were 500-1000 nm thick, optically-clear, crack-free, and with root mean square (RMS) surface roughness of ~1.2 nm measured by atomic force microscopy (AFM).

Example 3

HO-PMO Films with Various Organic Content with $Si_3(CH_2)_3$ Rings and $SiO_4$ Tetrahedra as Building Units Films of different organic content were made by mixing relative amounts of the silica precursor tetramethylorthosilicate (TMOS, 98% Aldrich) and $[(EtO)_2SiCH_2]_3$ with molar ratios n (TMOS): {n (TMOS)+n ($[(EtO)_2SiCH_2]_3$)}=0, 0.143, 0.333, 0.600 and 1 corresponding to the molar fraction f of the constituting Si sites f=D:(D+Q)=0, 0.25, 0.5, 0.75 and 1. The synthesis conditions of example 2 were employed.

Characterization of the High Organic Group Content Periodic Mesoporous Organosilica of Example 2 and 3

Figures 4A, 4B:
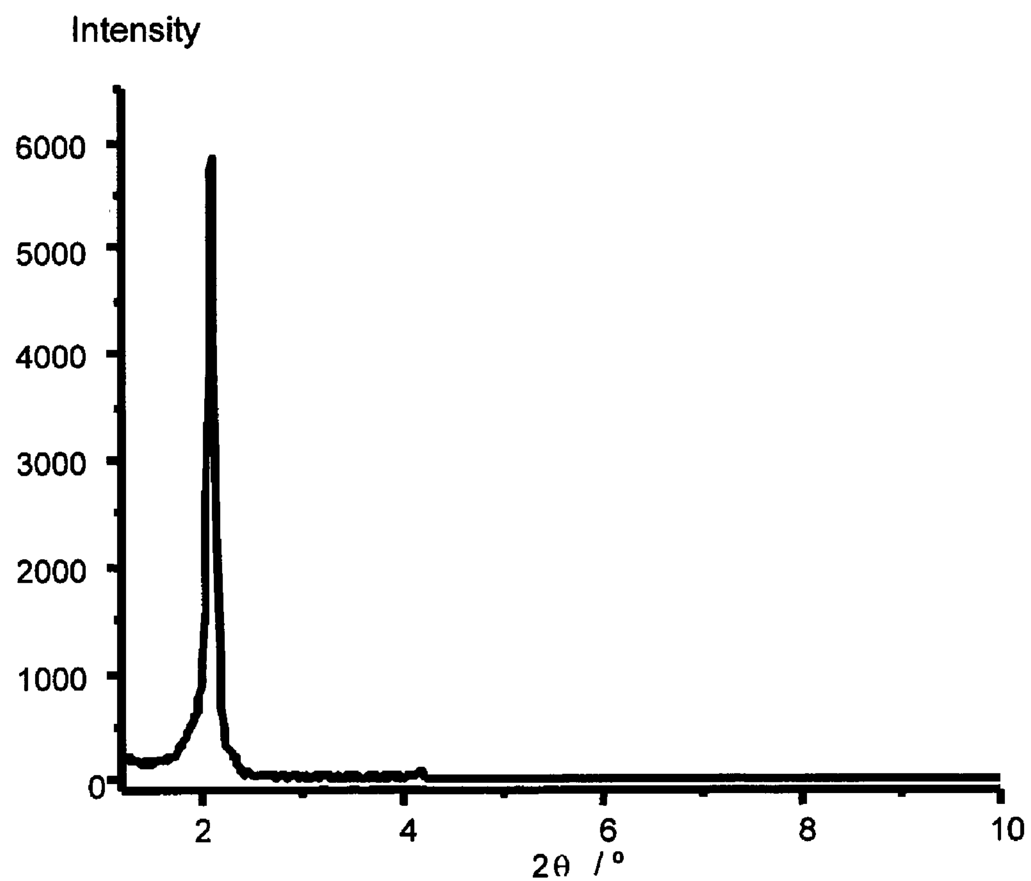
FIG. 4A shows an SEM mage of calcined PMO film.
FIG. 4B shows a PXRD image of calcined PMO film composed of $[SiCH_2]_3$ rings of FIG. 4A.
Figure 4C:
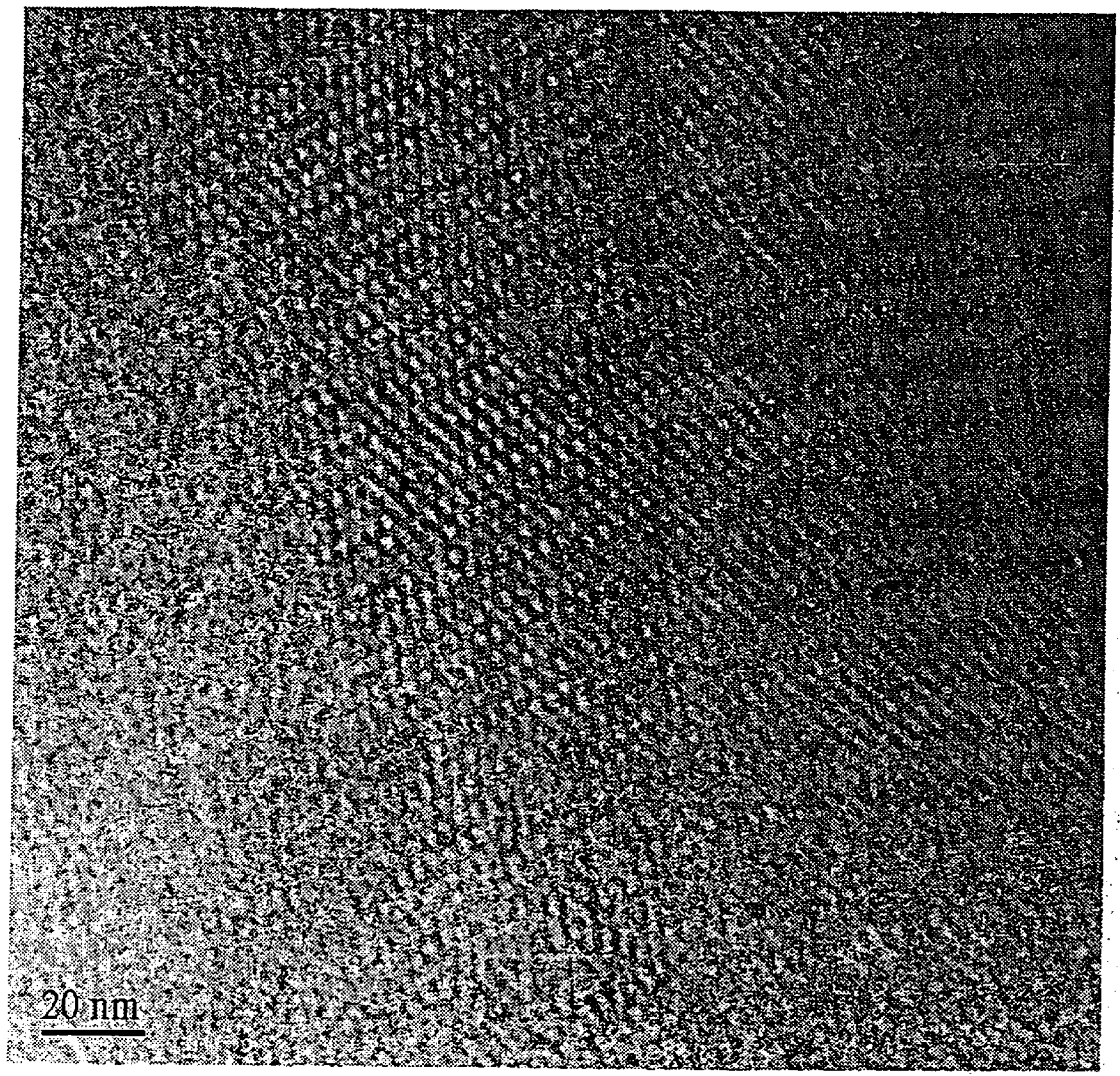
FIG. 4C shows a bright-field TEM image of calcined PMO film composed of $[SiCH_2]_3$ rings.
Figure 4D:
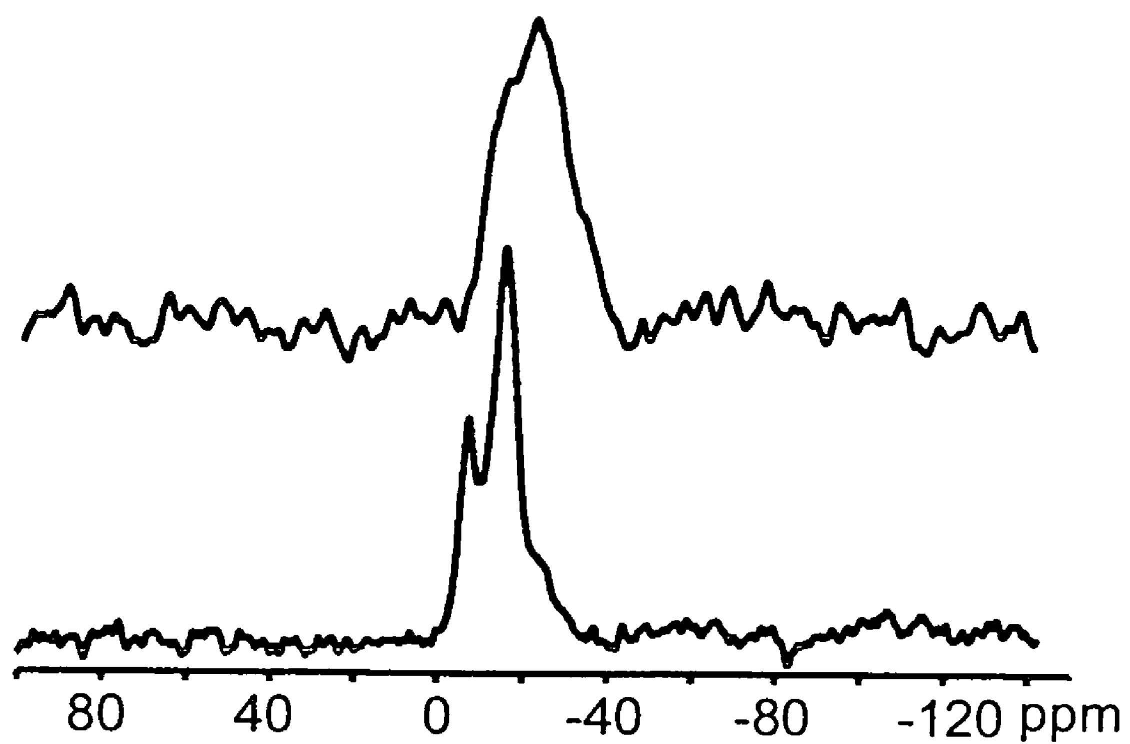
FIG. 4D shows $^{29}$Si MAS NMR spectra of powdered PMO films composed of $[SiCH_2]_3$ rings, as-synthesized and calcined at 300° C.

The PMOs that were obtained as a supported oriented film by spin coating onto a glass slide and calcined at 300° C. under $N_2$ atmosphere were characterized as follows: Calcined films were obtained without cracking or loss of mesostructure, as determined by scanning electron microscopy SEM, powder x-ray diffraction PXRD and TEM (FIGS. 4A-4C). In order to ensure the $CH_2$ bridge-bonded groups remained intact inside the channel walls after spin coating, 50 thin film samples were prepared on glass substrates (with area 2×2 cm). Half the films were scratched off the substrate and powdered to give a 25 mg sample, which was then investigated by $^{29}$Si MAS-NMR. These samples showed only $D_0$ and $D_1$ sites at −7 and −16 ppm as well as a shoulder at −24 ppm for some $D_2$ sites respectively, (FIG. 4D) thereby confirming the Si—C bonds were not cleaved in the self-assembly synthesis and film forming process. The other half of the films were calcined at 300° C. under $N_2$, then scratched off the substrate and investigated by $^{29}$Si NMR spectroscopy. The $^{29}$Si NMR spectrum showed a broadened signal at −20 ppm attributed to a convolution of $D_1$ and $D_2$ sites, proving that all Si—C bonds remained intact with further polymerisation of the organosilica framework compared to the as-synthesized film (FIG. 4D).

Dielectric and Mechanical Properties of the High Organic Group Content Periodic Mesoporous Organosilica Films of Examples 2 and 3

Films with varying organic content were synthesized using mixtures of the silica (tetramethylorthosilicate, TMOS) and the 3-ring $[(EtO)_2SiCH_2]_3$ precursor to give films with corresponding molar fractions (f) of Si sites, where f=D:(D+Q)=0, 0.25, 0.5, 0.75, and 1 (D=number of $SiC_2O_2$, Q=number of $SiO_4$ units) represents the organic group content.

A linear dependency of the $d_{100}$ channel spacing on the molar fraction f was observed for the films, indicating a compositional homogeneity in accordance with Vegard's law. The relative permittivity, or dielectric constant (k), was calculated from parallel-plate capacitance measurements of the films.

Figure 9:
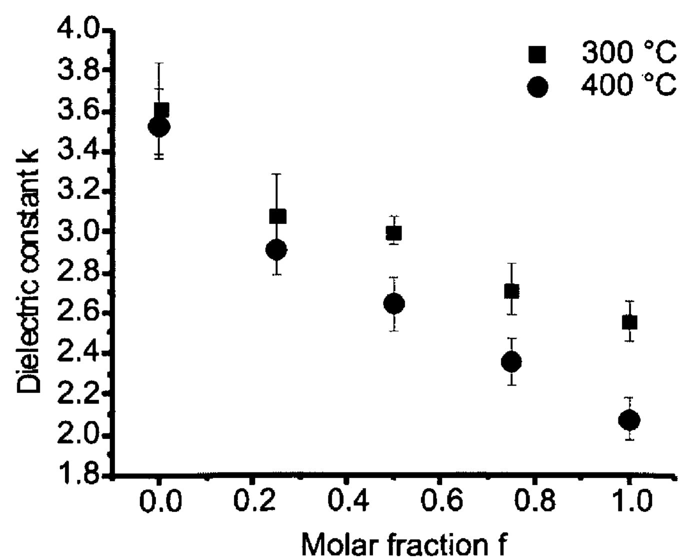
FIG. 9 shows the dielectric constants for HO-PMO films prepared from $TMOS/[EtO_2SiCH_2]_3$ mixtures with different molar fractions f of Q ($SiO_4$) and D ($SiO_2C_2$) silicon sites, where (f=D:(D+Q)) represents the organic group content. Black squares represent k for films treated for 5 h at 300° C. in a $N_2$ atmosphere before measurement, and the black circles represent k of the same samples treated for an additional 2 h at 400° C., having D sites partially converted into T sites with terminal $CH_3$ groups.

FIG. 9 shows the dielectric constants for films from TMOS/$[EtO_2SiCH_2]_3$ mixtures with different molar fractions f of Q ($SiO_4$) and D ($SiO_2C_2$) silicon sites, where (f=D:(D+Q)) represents the organic group content. Black squares represent k for films treated for 5 h at 300° C. in a $N_2$ atmosphere before measurement, and the black circles represent k of the same samples treated for an additional 2 h at 400° C., having D sites partially converted into T sites with terminal $CH_3$ groups. Films calcined at 300° C. under $N_2$, with all bridging organics preserved, showed a linear decrease of k with increasing organic group content, with k values around 2.5 for films made entirely from $[(EtO)_2SiCH_2]_3$ (ie; f=1.0). In addition, k of films with molar fractions f>0.5 changed little after exposure to air of 60% relative humidity for 2 hours, while k for films with fractions less than 0.5 increased significantly. The same film samples heated to 400° C. under $N_2$, to intentionally cause silanol-eliminating transformation from bridging methene to terminal methyl groups (partial D to T site conversion), showed k values further reduced to as low as k=2.0 for the films made entirely from $[(EtO)_2SiCH_2]_3$ (FIG. 9). Nanoindentation measurements yielded elastic modulus values of the film samples and show a small linear increase with f compared to pure mesoporous silica, from 8.7 GPa (f=0) to 11.8 GPa (f=1), indicating that these films may also have sufficient mechanical stability for low-k microelectronic applications.

Example 4

Synthesis of 3-Ring Substituted $[(EtO)_2SiCH_2]_2[(EtO)_2SiCHR]$ (R=I, Br, Et)

$[(EtO)_2SiCH_2]_3$ (7.2 mmol, 3 g) was dissolved in 200 ml THF (dried over Na/benzophenone) in a 1 liter 3 necked flask under nitrogen and cooled down to −78° C. in a dry ice/acetone bath. A 1.7 M solution of t-BuLi (8 mmol, 4.8 ml, Aldrich) was added drop-wise and the mixture was stirred for 30 min. A solution of $I_2$ (8 mmol, 2.03 g, 99+%, Aldrich) in 50 ml THF was added drop-wise. In the case of the bromo and ethyl substituted rings, $Br_2$ (8 mmol, 1.28 g, 99.+%, Aldrich) and iodoethane (8 mmol, 1.17 g, 99%, Aldrich) was used. The solution was slowly warmed up to room temperature and stirred for 3 h. The solvent was subsequently removed in a rotary evaporator. 200 ml pentane (anhydrous, 99+%, Aldrich) was added and the mixture was filtered. The pentane was evaporated from the filtrate and the residue was distilled under vacuum to give the desired pure product: $[(EtO)_2SiCH_2]_2[(EtO)_2SiCHI]$: 60% yield (b.p. 120° C. at 20 mTorr). $^{13}$C (300 MHz, $CDCl_3$): δ 59.11 (s, $CH_2$), 58.92 (s, $CH_2$), 58.20 (s, $CH_2$), 58.08 (s, $CH_2$), 18.20 (s, $CH_3$), 18.13 (s, $CH_3$), 18.09 (s, $CH_3$) 18.06 (s, $CH_3$), −3.58 (s, $CH_2$), −12.72 (CHI). $^1$H (300 MHz, $CDCl_3$): δ 3.6-3.9 (12H, m), 1.9 (1H, m), 1.1-1.3 (18H, m), 0-0.5 (4H, m). $[(EtO)_2SiCH_2]_2[(EtO)_2SiCHBr]$: 80% yield (b.p. 110° C. at 20 mTorr). $^{13}$C (300 MHz, $CDCl_3$): δ 59.10 (s, $CH_2$), 58.92 (s, $CH_2$), 58.22 (s, $CH_2$), 58.08 (s, $CH_2$), 18.24 (s, $CH_3$), 18.15 (s, $CH_3$), 18.11 (s, $CH_3$) 18.06 (s, $CH_3$), −3.58 (s, $CH_2$), 16.65 (CHBr). $^1$H (300 MHz, $CDCl_3$): δ3.7-4.0 (12H, m), 2.43 (1H, m), 1.2-1.4 (18H, m), 0-0.4 (4H, m). $[(EtO)_2SiCH_2]_2[(EtO)_2SiCHEt]$: (b.p. 88° C. at 20 mTorr). $^{13}$C (300 MHz, $CDCl_3$): δ 58.21 (s, $CH_2$), 58.00 (s, $CH_2$), 57.97 (s, $CH_2$), 57.94 (s, $CH_2$), 18.23 (s, $CH_3$), 17.47 (s, CH), 16.67 (s, $CH_2$) 16.34 (s, $CH_2$), −1.7 (s, $CH_2$). $^1$H (300 MHz, $CDCl_3$): δ 3.7-3.9 (12H, m), 1.67 (2H, quint.), 1.18-1.27 (18H, m), 1.07 (3H, t), 0.02-0.25 (5H, m).

Synthesis of 3-ring substituted HO-PMO from $[(EtO)_2SiCH_2]_2[(EtO)_2SiCHR]$ (R=Br, I, Et)

NaCl (25.8 mmol, 1.85 g) and 0.336 g Pluronic 123 (BASF) were dissolved in 2 N HCl (8.4 g) and $H_2O$ (155 mmol, 2.8 g). To this solution $[(EtO)_2SiCH_2]_2[(EtO)_2SiCHR]$ (0.84 mmol) was added under vigorous stirring at room temperature. The mixture was stirred at room temperature for 24 h while a white precipitate formed and kept under static conditions for another 48 h at 80° C. After filtration the HO-PMO was obtained as a white powder. The extraction was carried out by stirring the as-synthesized HO-PMOs in a mixture of 250 ml acetone and 10 ml 2N HCl for 4 d. The extraction was carried out at room temperature in the case of the Br and I substituted HO-PMOs to minimize the reactivity of the halogen groups, while the extraction of the ethyl substituted HO-PMOs was performed at 50° C. After the extraction the product was filtered off and washed with acetone. The described extraction was repeated 3 times.

Characterization of the High Organic Group Content Periodic Mesoporous Organosilica of Example 4

Figure 6:
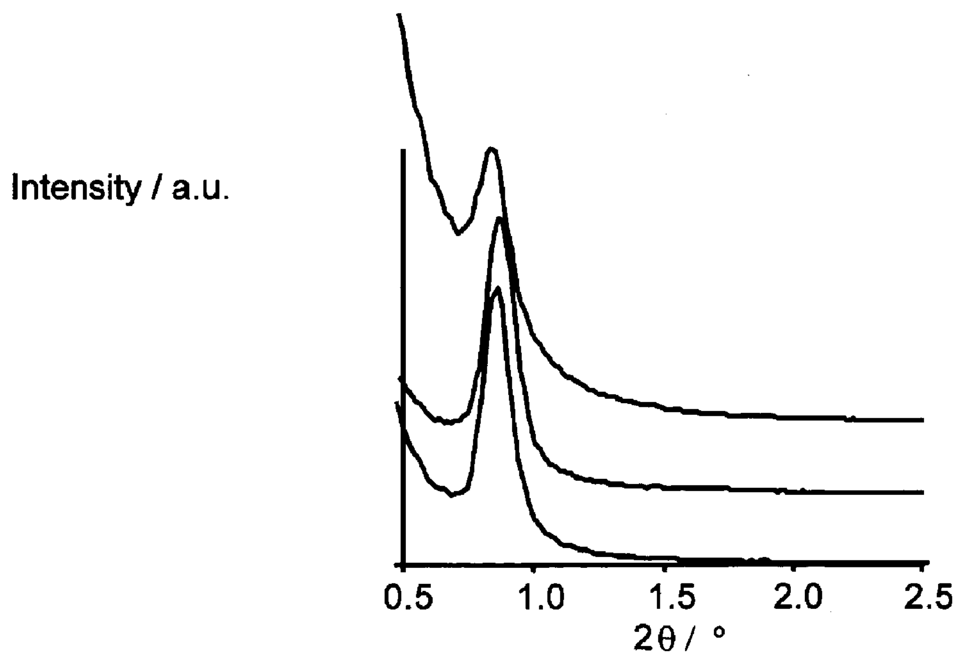
FIG. 6 shows PXRD patterns of the extracted PMOs composed of iodo, bromo and ethyl substituted rings $[Si(CH_2)]_2[Si(CHX)]$ (X=1, Br, Et)
Figure 7A:
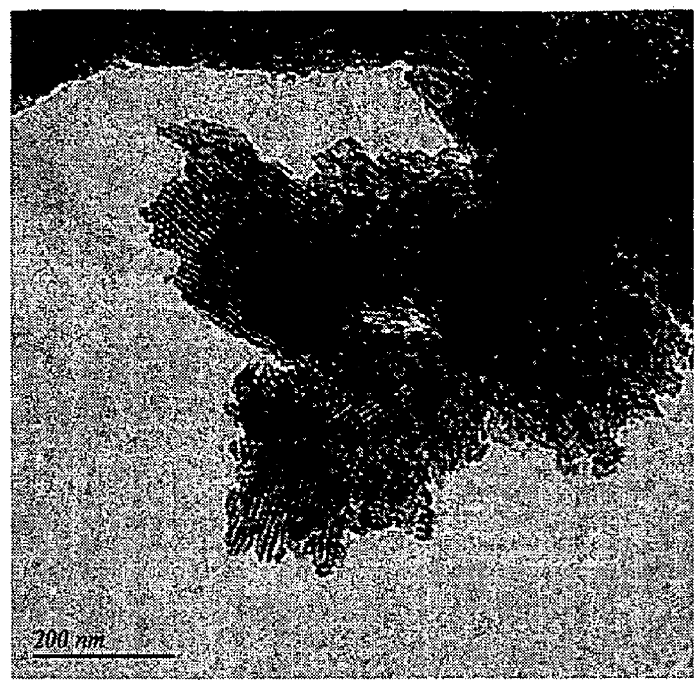
FIG. 7A shows bright-field TEM images of the as-prepared PMOs composed of iodo substituted rings $Si(CH_2)]_2[Si(CHI)]$.
Figure 7B:
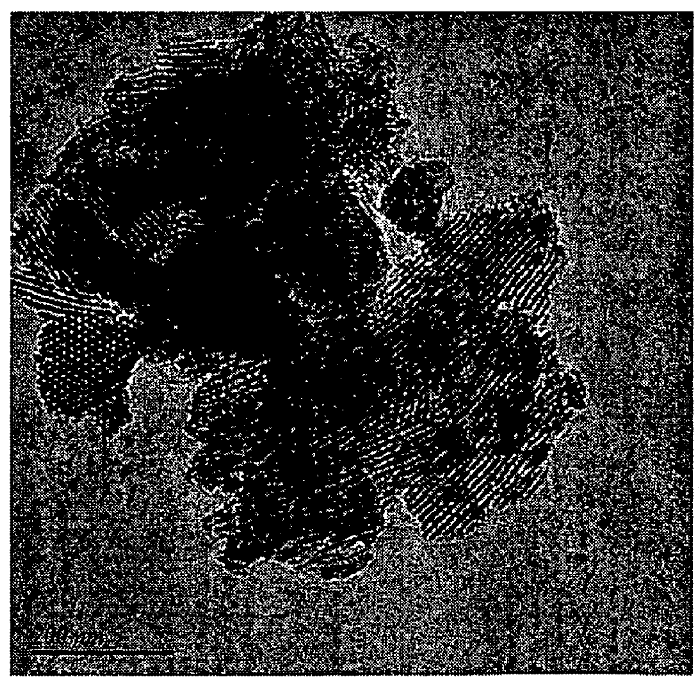
FIG. 7B shows bright-field TEM images of the as-prepared PMO composed of $Si(CH_2)]_2[Si(CHBr)]$.
Figure 7C:
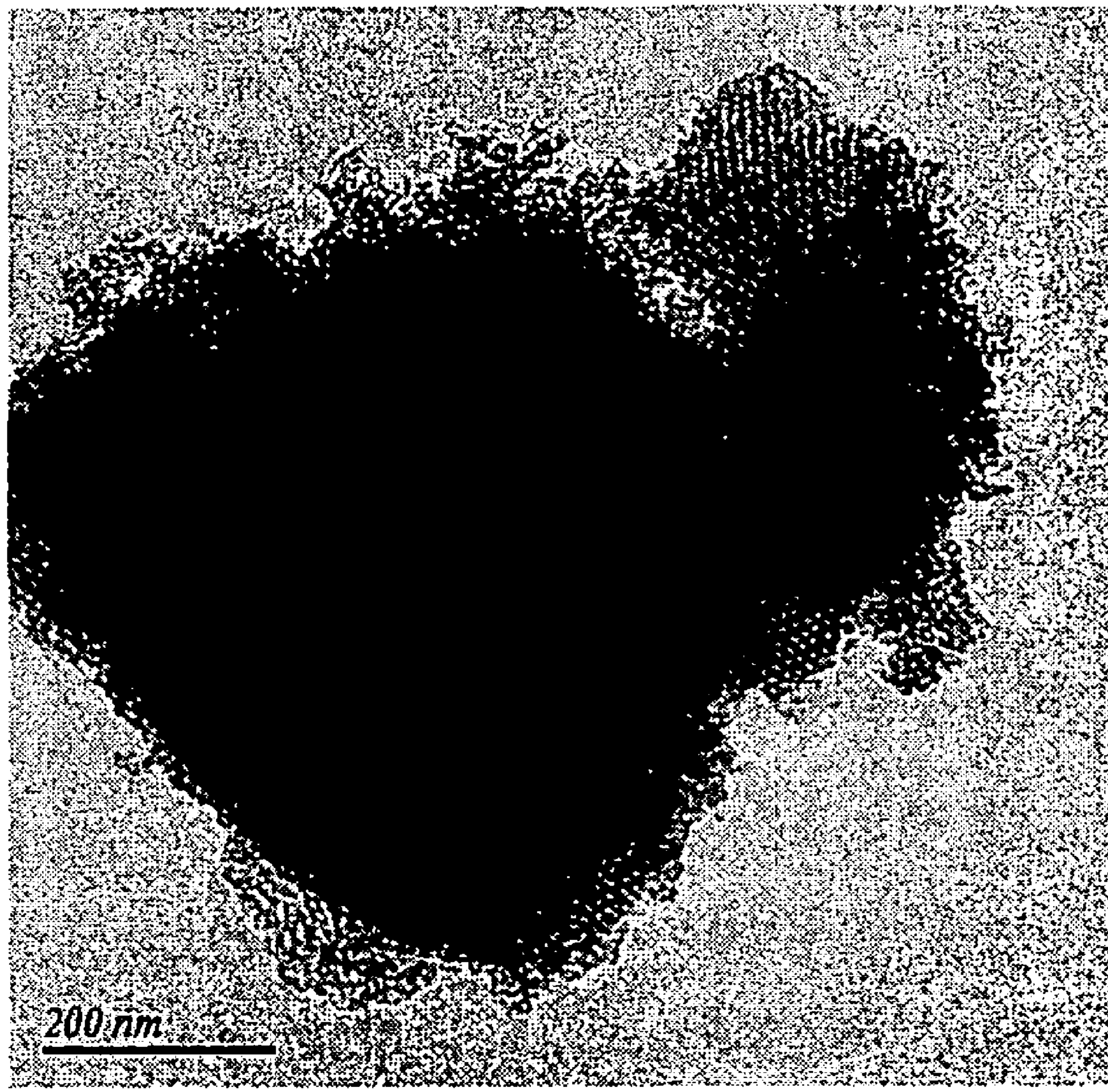
FIG. 7C shows bright-field TEM images of the as-prepared PMOs composed of $Si(CH_2)]_2[Si(CHEt)]$.

FIG. 6 shows PXRD patterns of the extracted iodo, bromo and ethyl substituted PMOs. From FIG. 6 it can be seen that the high organic group content PMOs obtained from 2, 3, and 4 were well ordered with a diagnostic d-spacing of 10.1 nm for R=Br, 10.3 nm (R=I), and 10.5 nm (R=Et) according to PXRD. FIG. 7A shows bright-field TEM images of the as-prepared iodo substituted PMOs, FIG. 7B shows bright-field TEM images of the as-prepared bromo substituted PMOs, and FIG. 7C shows bright-field TEM images of the as-prepared ethyl substituted PMOs. These TEM measurements of FIGS. 7A to 7C corroborate the bulk measurements giving additionally a pore wall thickness of about 6 nm and pore sizes of about 4.5 nm.

Figure 8:
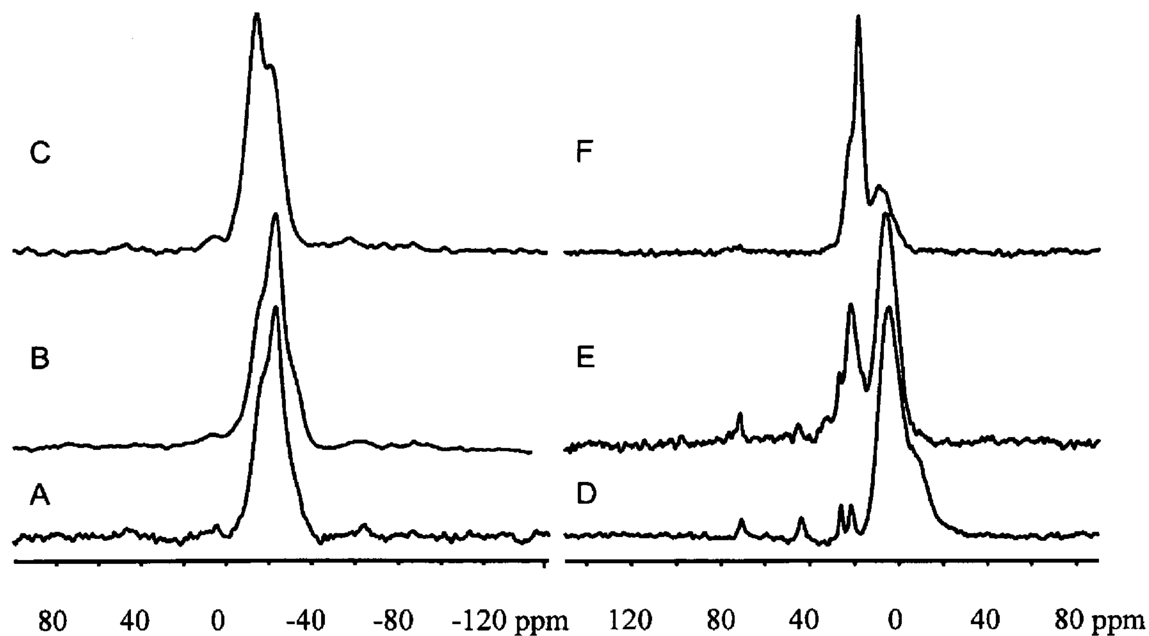
FIG. 8 shows $^{29}$Si CP MAS NMR (A-C) and $^{13}$C CP MAS NMR spectra (D-F) of the extracted PMOs composed of $Si(CH_2)]_2[Si(CHX)]$ rings in which the $^{29}$Si signals (A: X=I, δ=−23 ppm, B: X=Br, δ=−25 ppm; C: X=Et, δ=−15 ppm, δ=−24 ppm) can be assigned to D ($SiO_2C_2$) sites.

FIG. 8 shows $^{29}$Si CP MAS NMR (A-C) and $^{13}$C CP MAS NMR spectra (D-F) of the R substituted extracted PMOs in which the $^{29}$Si signals (A: R=I, δ=−23 ppm, B: R=Br, δ=−25 ppm; C: R=Et, δ=−15 ppm, δ=−24 ppm) can be assigned to D ($SiO_2C_2$) sites. These $^{29}$Si CP MAS NMR experiments showed that no significant Si—C bond cleavage occurred during synthesis. The respective $^{13}$C CP MAS NMR spectra of FIG. 8 further indicated that the majority of the groups R(R=I, Br, Et) remained intact after synthesis and extraction as the chemical shifts for the major signals of the $^{13}$C nuclei bound to R in both the PMO and the precursor molecule are similar.

The $^{13}$C spectrum for the iodo substituted ring PMO (D) shows one signal for the $CH_2$ groups at 4 ppm with a broad shoulder around −5 ppm, that can be assigned to the CHI groups. Similarly, the $^{13}$C spectrum for the PMO with R=Br (E) shows a signal at 6 ppm for the $CH_2$ groups and a signal at 21 ppm that can be assigned to the CHBr units. In the spectrum for the PMO with ethyl side groups (F) the $CH_2$ groups can be seen at 9 ppm with the signals for the CH-Et units appearing between 18 and 20 ppm. Furthermore small signals around 70 ppm were observed for all $^{13}$C spectra that can be attributed to the surfactant, which remained in small amounts inside the pores despite long extraction times.

The small resonances at 43 and 25 ppm in the spectra of FIG. 8 suggests little substitution of the halogen atoms for the bromo- and iodo substituted ring PMOs, presumably by OH and Cl. The small signal at 21 ppm can be assigned to the middle $CH_2$ group of the surfactant's propylene blocks. To confirm this a $^{13}$C CP MAS NMR spectrum of the pure tri-blockcopolymer P123 was taken showing signals around 70 ppm for the O—$CH_2$—C units of both the ethylene and propylene blocks and 21 ppm for the C—$CH_2$—C units of the propylene blocks. The presence of large amounts of Br and I in the respective substituted ring PMOs was also established by EDX measurements suggesting that most of the C—Br and the C—I groups are intact in the material.

Example 5

Synthesis of $\{[(EtO)_2SiCH_2]_2[(EtO)_2SiCH]\}_2\{(CH_2)_3\}$ $[(EtO)_2SiCH_2]_3$ (7.5 mmol, 3 g) was dissolved in 200 ml THF (dried over Na/benzophenone) in a 1 liter 3 necked flask under nitrogen and cooled down to −78° C. in a dry ice/acetone bath. A 1.7 M solution of t-BuLi (8.25 mmol, 4.8 ml, Aldrich) was added drop-wise and the mixture was stirred for 30 min. Then 1,3-dibromopropane (3.75 mmol, 0.38 ml, Aldrich) was added drop-wise. The solution was slowly warmed up to room temperature and stirred for 2 d. Then the solvent was removed in a rotary evaporator. 200 ml pentane (anhydrous, 99+%, Aldrich) was added then and the mixture was filtered. The pentane was evaporated from the filtrate and the residue was distilled under high vacuum. The third fraction gave the desired pure product. $\{[(EtO)_2SiCH_2]_2[(EtO)_2SiCH]\}_2\{(CH_2)_3\}$: 30% yield (b.p. 145° C. at 20 mTorr). 13C (300 MHz, $CDCl_3$): δ 58.36 (s, $CH_2$), 58.21 (s, $CH_2$), 58.17 (s, $CH_2$), 58.13 (s, $CH_2$), 18.41-18.48 (m, $CH_3$), 36.44 (s, $CH_2$), 23.93 (s, $CH_2$), 14.27 (s, CH), −1.61 (s, $CH_2$). $^{1}$H (300 MHz, $CDCl_3$): δ 3.65-3.85 (24H, m), 1.45-1.6 (2H, m), 1.1-1.25 (38H, m), 0.15-0.3 (2H, m), 0-0.1 (8H, m). $^{29}$Si (400 MHz, $CDCl_3$): −8.1 (s), −9.0 (s). MS (ESI) (m/z)=832 (100%).

Synthesis of propane-1,3diyl Bridged 3-Ring Periodic Mesoporous Organosilica (PMO)

NaCl (25.8 mmol, 1.85 g) and 0.336 g Pluronic 123 (BASF) were dissolved in 2 N HCl (8.4 g) and $H_2O$ (155 mmol, 2.8 g). To this solution 1 (0.84 mmol, 0.7 g) was added with vigorous stirring at room temperature. The mixture was stirred at room temperature for 24 h while a white precipitate formed and kept under static conditions for another 48 h at 80° C. After filtration the PMO was obtained as a white powder. The extraction was carried out by stirring the as-synthesized PMOs in a mixture of 250 ml acetone and 10 ml 2N HCl for 2 d.

Characterization of the HO-PMO of Example 5

Figure 10A:
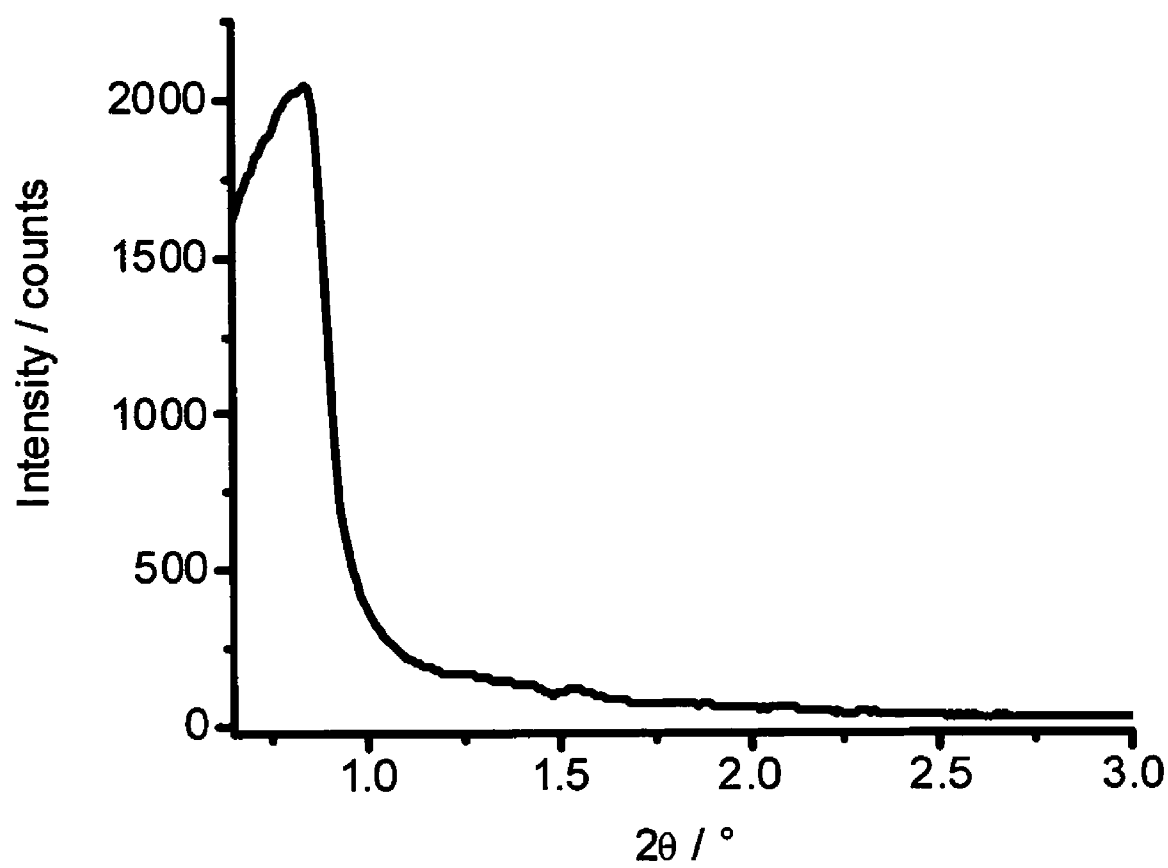
FIG. 10A shows the PXRD of the extracted PMO composed of propane-1,3-diyl bridged rings.
Figure 10B:
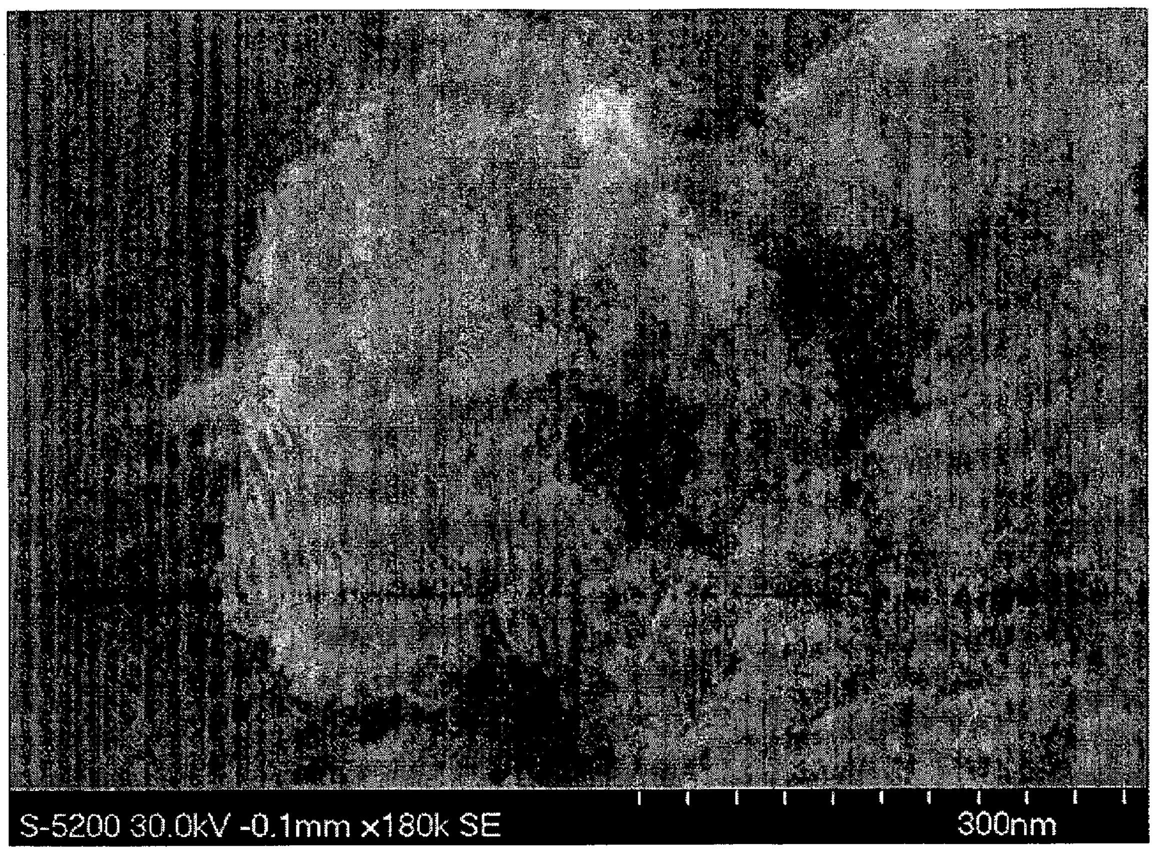
FIG. 10B is a SEM image of the PMO composed of propane-1,3-diyl bridged rings.
Figure 10C:
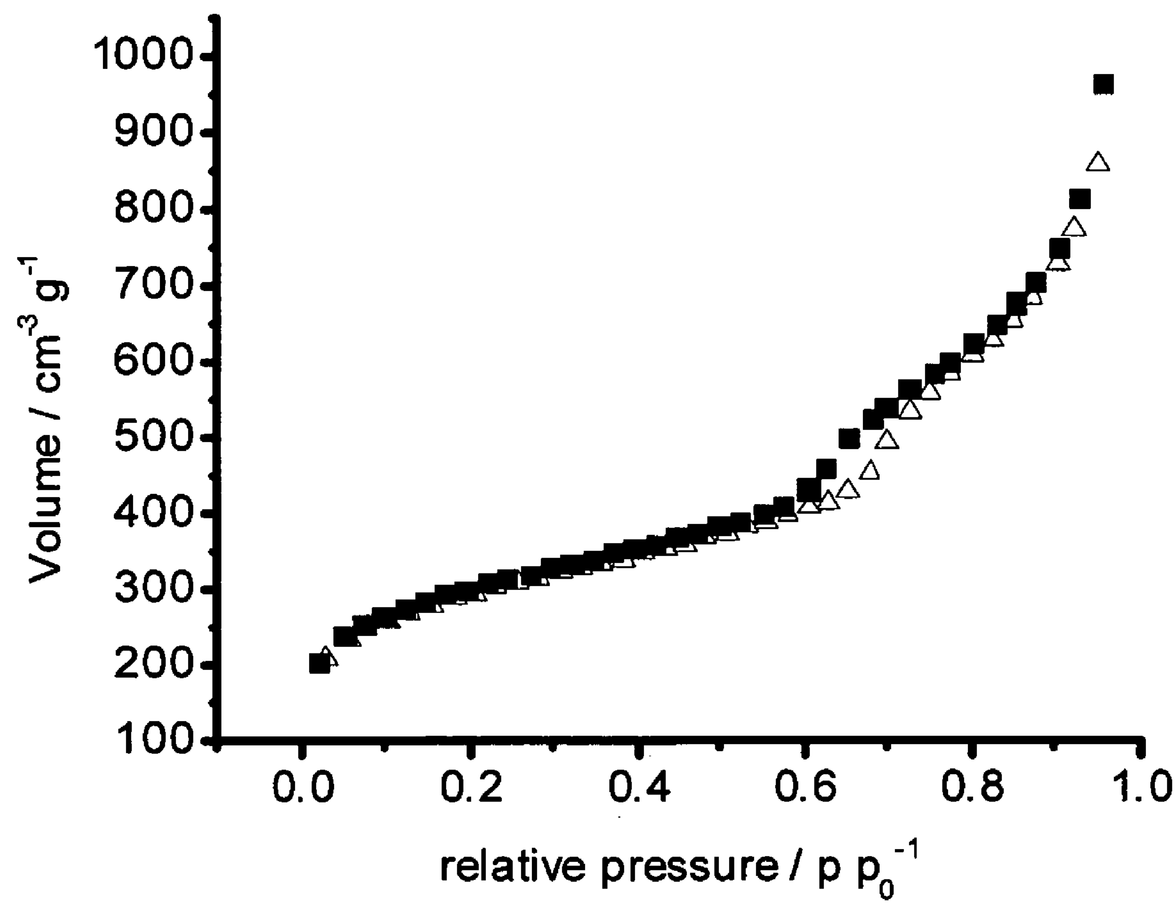
FIG. 10C shows the $N_2$ isotherm of the PMO composed of propane-1,3-diyl bridged ring with the pore size distribution as the inset.
Figure 10D:
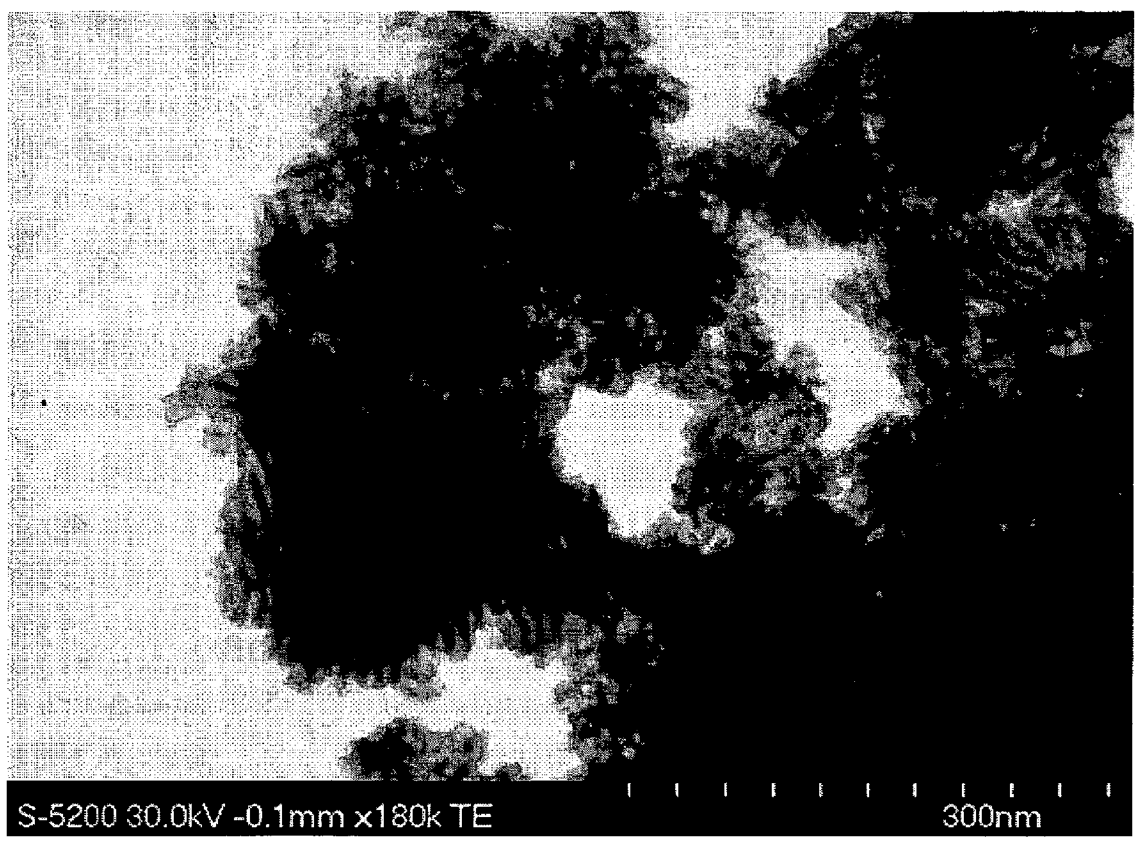
FIG. 10D is a TEM image of the PMO composed of propane-1,3-diyl bridged ring of FIG. 10B.

The resulting PMO shows periodic mesopores with a d spacing of 11.5 nm according to PXRD (FIG. 10A), a 6 nm pore-diameter and a channel wall thickness of also ca. 6 nm defined by SEM (FIG. 10B) and TEM (FIG. 10C). $N_2$ adsorption experiments revealed a type IV isotherm with minor hysteresis depicting the existence of highly uniform mesopores (FIG. 10D). BJH analysis of the adsorption branch showed a narrow pore size distribution with an average pore size of 6.9 nm consistent with the TEM data (FIG. 10D, inset). The PMO material displayed excellent thermal stability with no mass loss up to 400° C. in a $N_2$ atmosphere according to TGA experiments.

Figure 11:
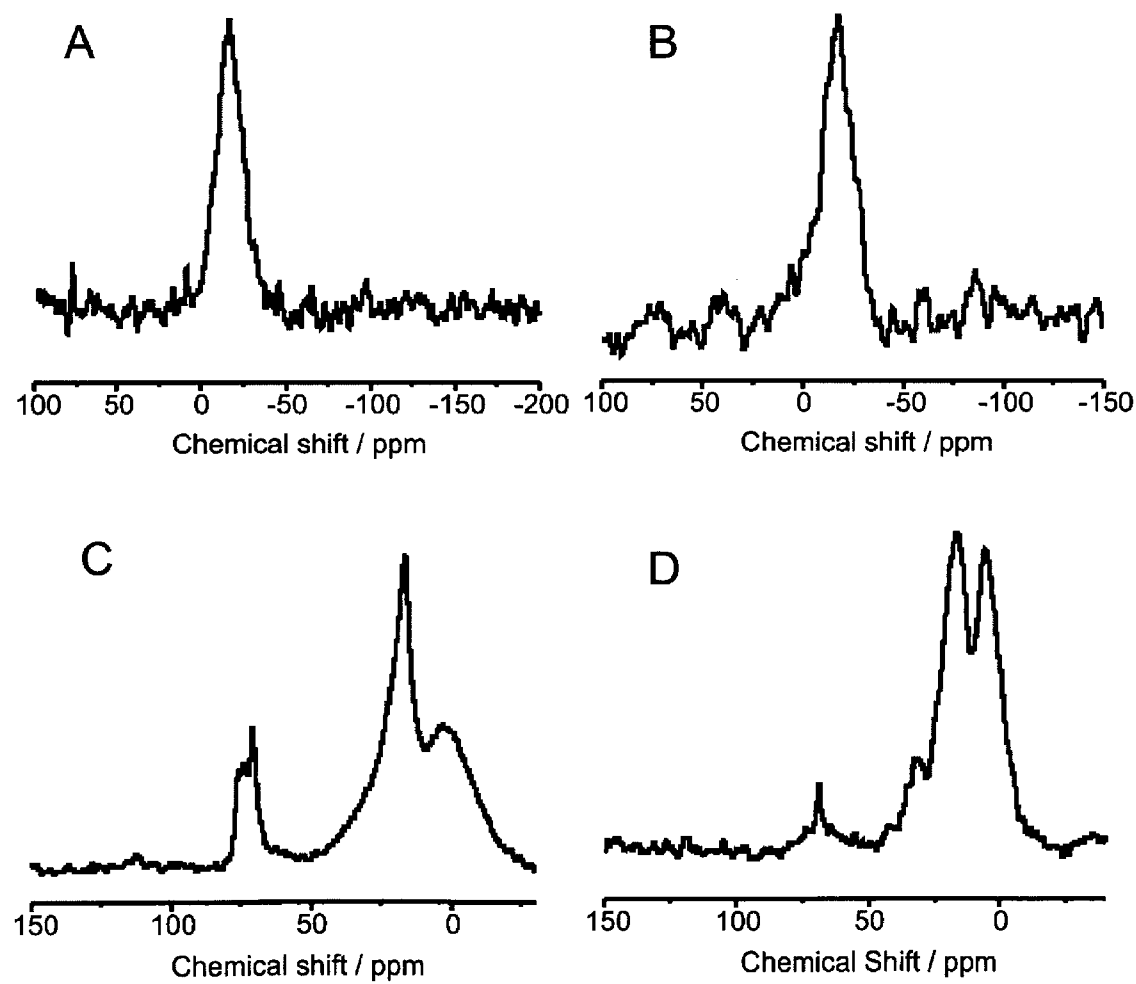
FIG. 11A shows the $^{29}$Si MAS NMR of the as-synthesized PMO composed of propane-1,3-diyl bridged rings.
FIG. 11B shows the respective spectrum for the extracted PMO composed of propane-1,3-diyl bridged rings.
FIG. 11C shows the $^{13}$C CP MAS NMR of the as-synthesized PMO composed of propane-1,3-diyl bridged rings.
FIG. 11D shows the respective spectrum for the extracted PMO composed of propane-1,3-diyl bridged ring.

$^{29}$Si MAS NMR data showed for both the as-synthesized (FIG. 11A) and the extracted PMO (FIG. 11B) a broad signal between 0 and 30 ppm that can be assigned to D sites of the $SiC_2O_2$ tetrahedra, which correspond well to the chemical shift of the $^{29}$Si signals (8.1 and 9.0 ppm) in the precursor molecule. The presence of the organic groups can be seen in the $^{13}$C CP MAS NMR spectra of the as-synthesized (FIG. 11C) and the extracted (FIG. 11D) samples. In the spectrum of the extracted material, three overlapping signals around 5, 17 and 32 ppm can be seen, which can be assigned to the propene group as well as the CH and $CH_2$ groups of the propene-bridged 3-ring units.

The peaks correspond well with the $^{13}$C signals at 36.4, 23.9 ppm ($CH_2$ groups of the propene bridge), 14.8 and −1.6 ppm (CH and $CH_2$ groups of the ring) of the precursor molecule. The weak signal at 69 ppm indicates that small amounts of P123 template remained after the extraction of the material. In the $^{13}$C spectrum of the as-synthesized PMO (FIG. 11C) the presence of the P123 template can be observed by strong peaks at 70, 73 and 75 ppm for the C atoms bound to 0 in the polyether.

The $CH_3$ groups of the 1,2-dioxopropene $OCH_2CH(CH_3)O$ groups of P123 that are known to exhibit a chemical shift around 20 ppm overlap with the signals of the organic bridging groups in the channel walls of the PMO explaining the difference between the spectra of the as-synthesized and the extracted PMO. The NMR data indicate that practically no Si—C bond cleavage has occurred in the PMO during either the self-assembly or the extraction process. In conclusion, the integrity of the propene-bridged 3-ring building block is maintained intact in the channel walls of the PMO.

Example 6

Synthesis of $\{[(EtO)_2SiCH_2]_2[(EtO)_2SiCH]\}_2\{(CH_2CHCHCH_2\}$ $[(EtO)_2SiCH_2]_3$ (7.5 mmol, 3 g) was dissolved in 200 ml THF (dried over Na/benzophenone) in a 1 liter 3 necked flask under nitrogen and cooled down to −78° C. in a dry ice/acetone bath. A 1.7 M solution of t-BuLi (8.25 mmol, 4.8 ml, Aldrich) was added drop-wise and the mixture was stirred for 30 min. Then 1,4-dibromo-2-butene (3.75 mmol, 0.38 ml, Aldrich) was added drop-wise. The solution was slowly warmed up to room temperature and stirred for 2 d. Then the solvent was removed in a rotary evaporator. 200 ml pentane (anhydrous, 99+%, Aldrich) was added then and the mixture was filtered. The pentane was evaporated from the filtrate and the residue was distilled under high vacuum. The third fraction gave the desired pure product.

$\{[(EtO)_2SiCH_2]_2[(EtO)_2SiCH]\}_2\{CH_2CHCHCH_2\}$: 50% yield (b.p. 200° C. at 20 mTorr). $^{13}C$ (300 MHz, $CDCl_3$): δ 131.62 (s, CH), 58.14 (s, $CH_2$), 57.98 (s, $CH_2$), 57.88 (s, $CH_2$), 18.21-18.18 (m, $CH_3$), 26.35 (s, $CH_2$), 23.93, 14.52 (s, CH), −1.57 (s, $CH_2$). $^1H$ (300 MHz, $CDCl_3$): δ 5.55-5.65 (2H), 3.65-3.85 (24H, m), 2.20-2.30 (4H, m), 1.10-1.30 (38H, m), 0.25-0.35 (2H, m), −0.1-0.2 (8H, m). $^{29}Si$ (400 MHz, $CDCl_3$): δ −8.42 (s), −9.25 (s). MS (ESI) (m/z)=844 (100

Synthesis of periodic mesoporous organosilica (PMO) from $\{[(EtO)_2SiCH_2]_2[(EtO)_2SiCH]\}_2\{(CH_2CHCHCH_2\}$ NaCl (25.8 mmol, 1.85 g) and 0.336 g Pluronic 123 (BASF) were dissolved in 2 N HCl (8.4 g) and $H_2O$ (155 mmol, 2.8 g). To this solution $\{[(EtO)_2SiCH_2]_2[(EtO)_2SiCH]\}_2\{(CH_2CHCHCH_2\}$ (0.43 mmol, 0.37 g) was added with vigorous stirring at room temperature. The mixture was stirred at room temperature for 24 h while a white precipitate formed and kept under static conditions for another 48 h at 80° C. After filtration the PMO was obtained as a white powder. The extraction was carried out by stirring the as-synthesized PMOs in a mixture of 250 ml acetone and 10 ml 2N HCl for 2 d.

Characterization of the HO-PMO Material of Example 6

Figure 12:
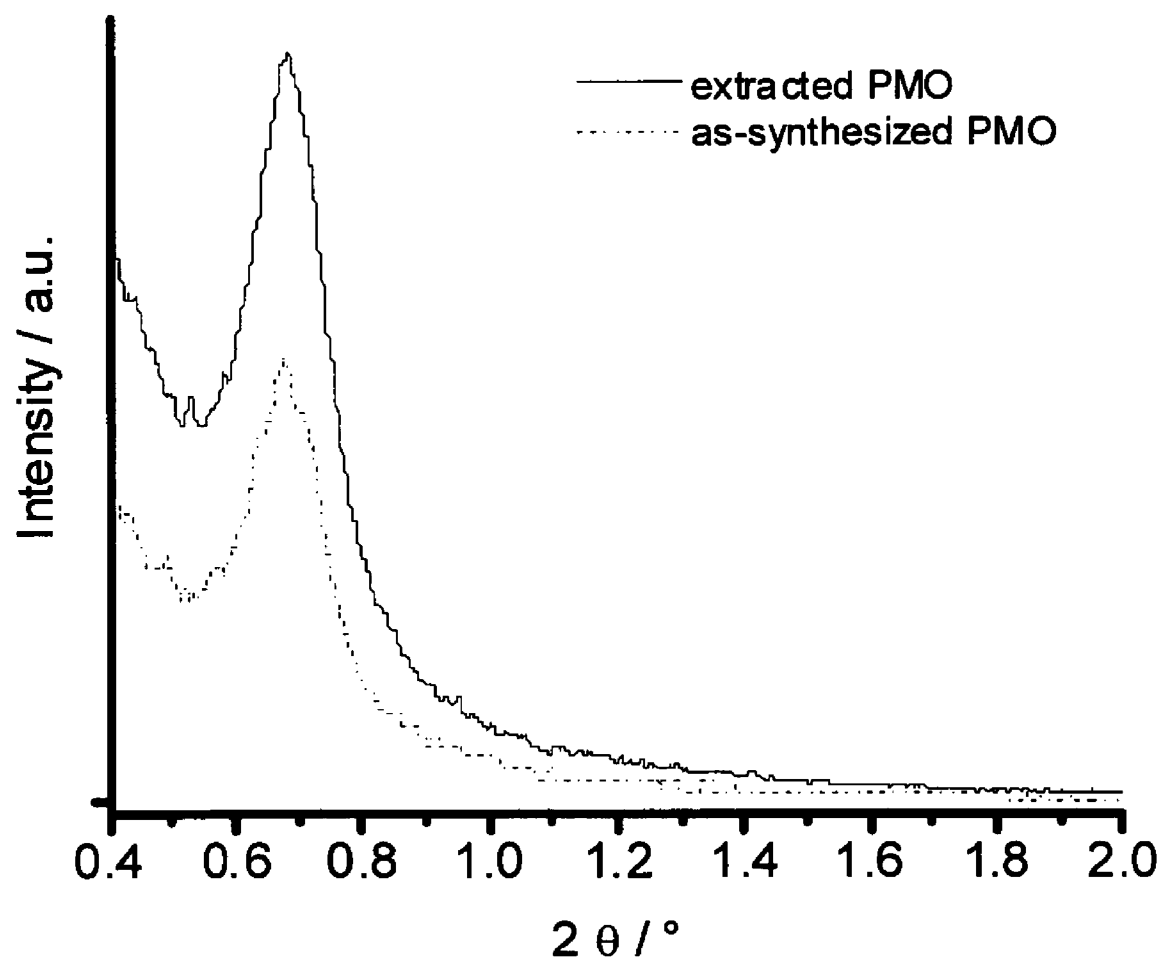
FIG. 12 shows the small angle X-ray diffraction pattern of the PMO materials built up from but-2-ene-1,4diyl bridged rings.

FIG. 12 shows the small angle X-ray diffraction pattern of the PMO materials built up from but-2-ene-1,4diyl bridged 3-rings (black: with the template; green: without template). These PXRD investigations showed the periodicity of the mesopores with a lattice d-spacing of 13.2 nm.

Figure 13A:
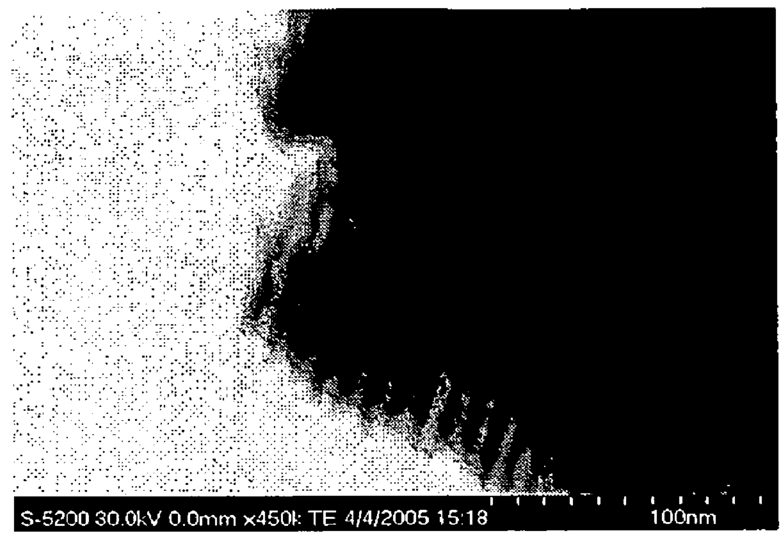
FIGS. 13A and 13D shows a TEM of the surfactant-free PMO material built up from but-2-ene-1,4diyl bridged rings.
Figure 13B:
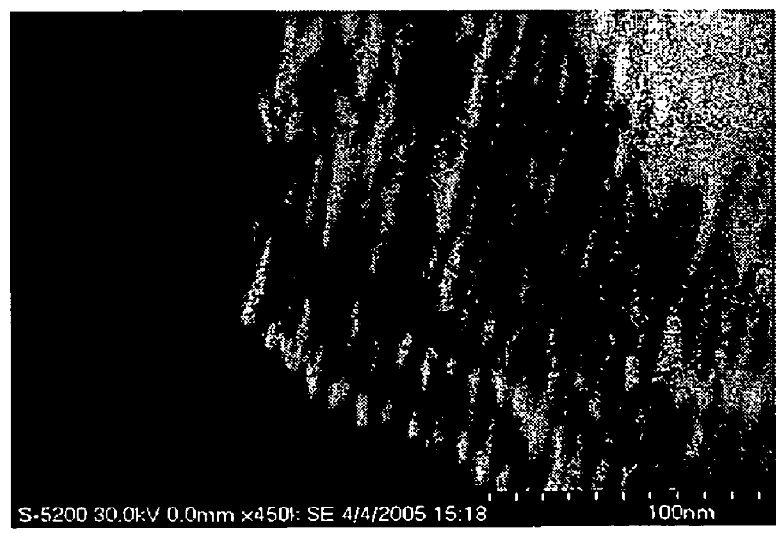
FIGS. 13B and 13C show an SEM of the surfactant-free PMO material built up from but-2-ene-1,4diyl bridged-rings.
Figure 13C:
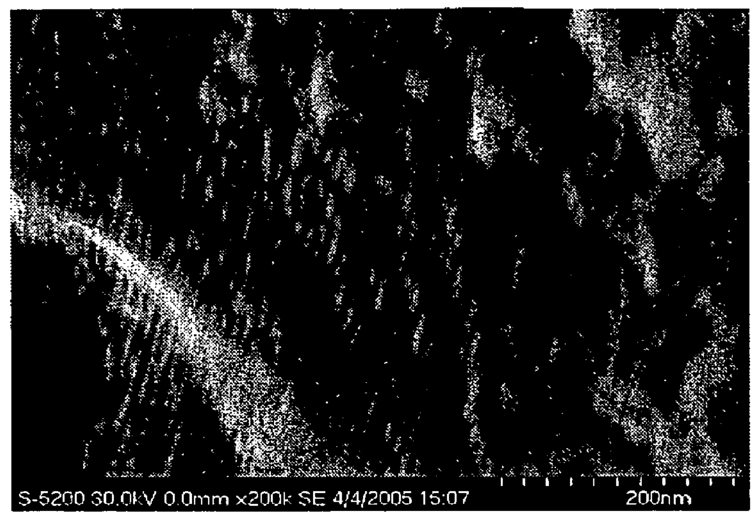
Figure 13D:
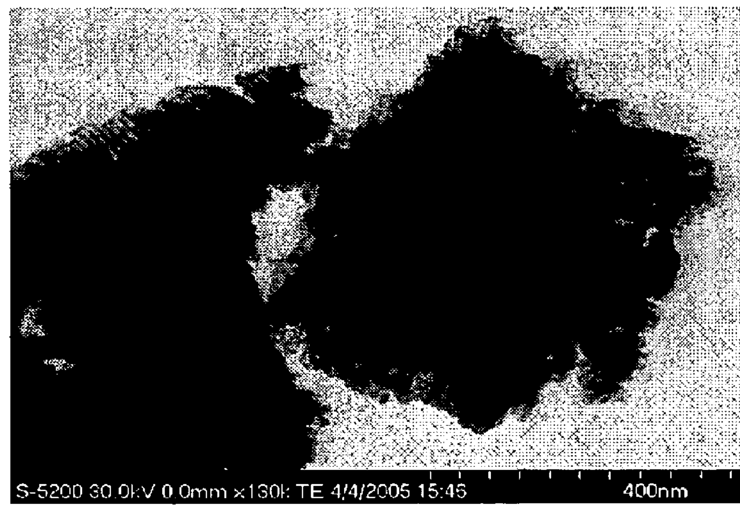
Figure 14:
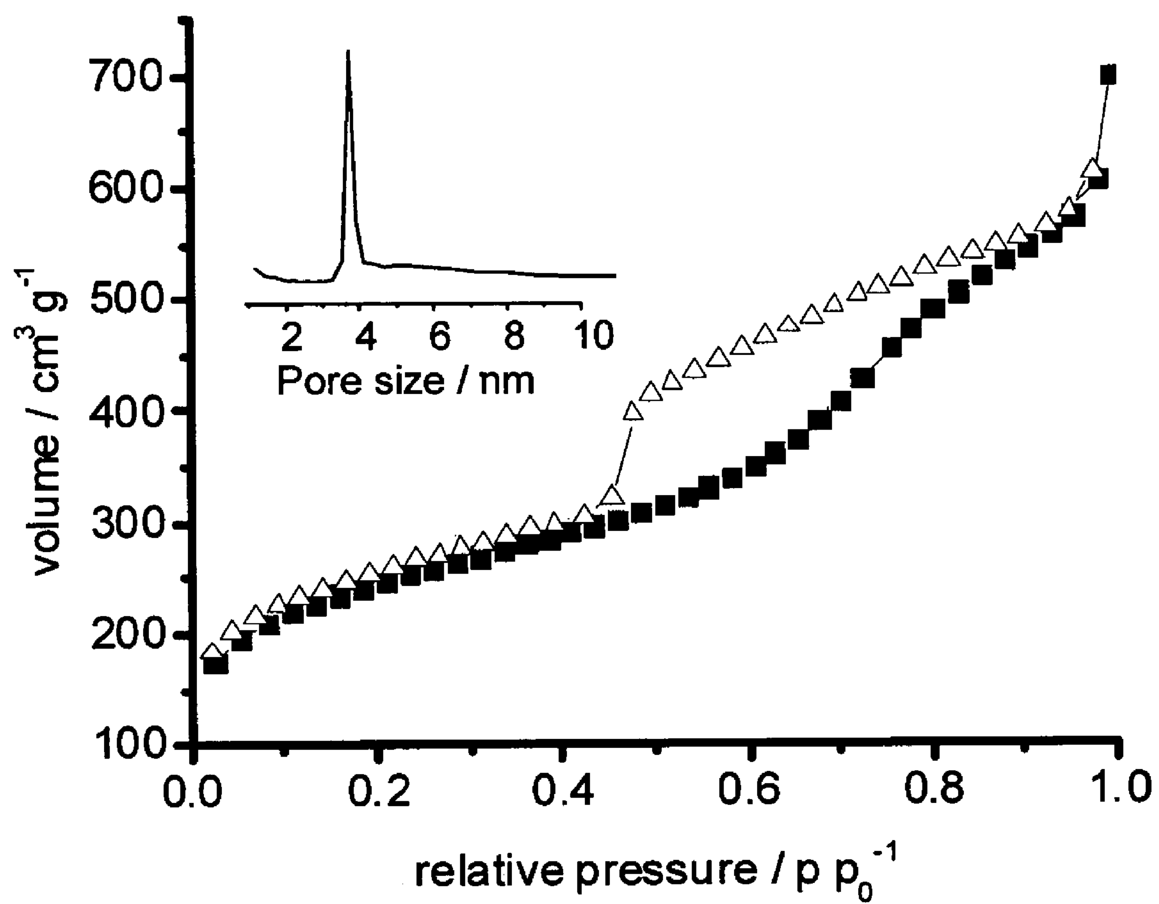
FIG. 14 shows a nitrogen adsorption isotherm of the surfactant-free PMO material built up from but-2-ene-1,4diyl bridged rings (inset: BJH pore size distribution taken from the desorption branch)
Figure 15A:
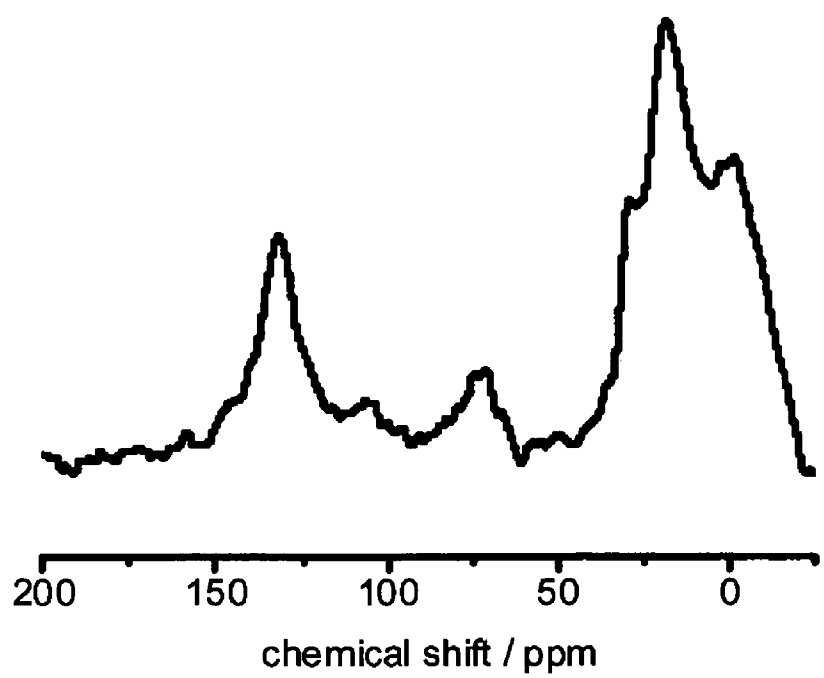
FIG. 15A shows a $^{13}$C CP MAS NMR of the extracted PMO form but-2-ene-1,4diyl bridged rings.
Figure 15B:
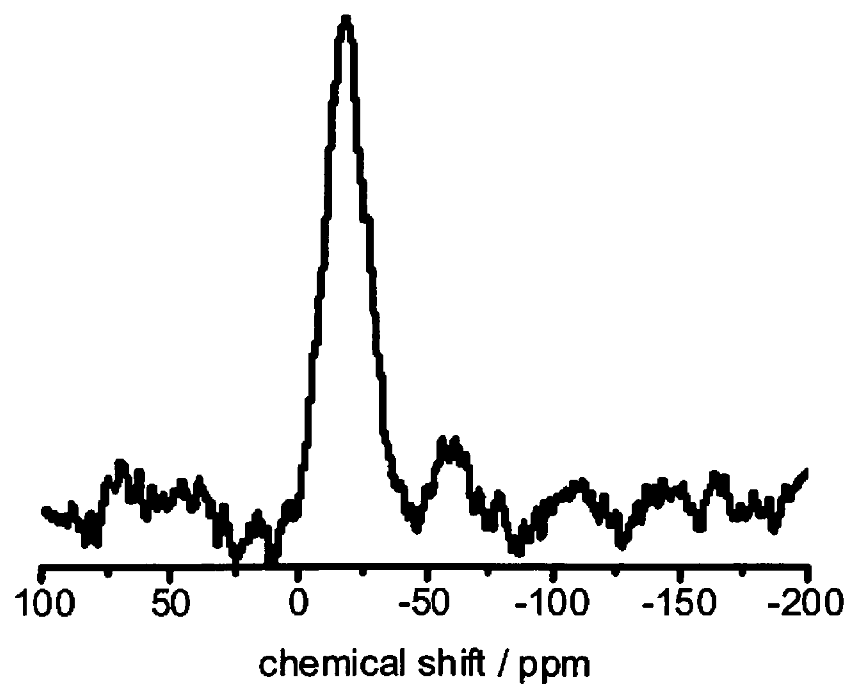
FIG. 15B shows a $^{29}$Si MAS NMR of the extracted PMO from but-2-ene-1,4diyl bridged rings.

FIGS. 13A and 13D shows a TEM of the surfactant-free PMO material built up from but-2-ene-1,4diyl bridged 3-rings, and FIGS. 13B and 13C show an SEM of the surfactant-free PMO material built up from but-2-ene-1,4diyl bridged 3-rings. These SEM and TEM investigations show that the PMO has ordered tubular uniform mesopores with a diameter of ca. 5 nm and channel walls of thickness ca. 8 nm. Referring to FIG. 14, $N_2$ sorption shows a typical type IV isotherm with a modest hysteresis and a narrow pore size distribution was revealed by BJH analysis. The BET surface area was found to be 804 $m^2\,g^{-1}$. $^{29}Si$ MAS NMR investigations shows a broad signal around −18 ppm, which can be assigned to D sites of $SiO_2(CH_2)_2$ tetrahedral units (FIG. 15B). This and the absence of signals for T and Q sites around −60 and −110 ppm suggests no significant Si—C bond cleavage has occurred during synthesis or template removal and that the bridged cyclic building units exclusively build up the framework of the material. $^{13}C$ CP MAS NMR of the extracted PMO shows three broad overlapping signals around −1.6, 18.5 and 28.6 ppm. (FIG. 15A).

Comparison with the $^{13}C$ NMR spectrum of the precursor molecule and the starting compound $[SiCH_2(OEt)_2]_3$ suggests that the signal at −1.6 can be assigned to the $CH_2$ groups of the rings while the signal at 18.5 likely corresponds to the CH group of the ring and the signal 28.6 ppm represents the $CH_2$ groups of the bridging but-2-ene-1,4-diyl groups. The signals for the unsaturated carbon atoms of the but-2-ene-1,4-diyl groups can be found at around 131.9 ppm. TGA measurements performed under nitrogen indicate a thermal stability of 380° C. showing no significant mass loss below this temperature.

Instrumentation Used for the Characterization of the HO-PMOs

PXRD patterns were measured with a Siemens D5000 diffractometer using Cu $K\alpha_1$-radiation (λ=154.18 pm) and a Bruker SAXS Nanostar. TEM images were recorded on a Philips 430 microscope operating at an accelerating voltage of 200 kV (film fragments on C film-coated Cu grids) or an Hitachi S-5200 STEM at 30 kV accelerating voltage. SEMs were also recorded by a Hitachi S-5200 SEM operating at 30 kV. All solid state NMR experiments were performed with a Bruker Avance DSX 400 NMR spectrometer. 29Si MAS-NMR spectra were recorded at a spin rate of 5 kHz and a pulse delay of 5 s. 13C CP MAS-NMR experiments were performed at a spin rate of 5 kHz, a contact time of 5 ms and a pulse delay of 3 s. TGA experiments were carried out with a Perkin-Elmer TGA7 instrument with a heating rate of 10° C./min. Sorption experiments were performed by a Quantachrome Autosorb-1C machine with $N_2$ as sorption gas at 77 K starting at a relative pressure p/p0=10−5. 7 data points were selected for BET analysis from relative pressure of 0.1. Capacitance measurements were made on films deposited on heavily-doped p-type Si (100) wafers (<1 Ωcm), with sputtered Au top electrodes (~0.6 $mm^2$), using a Hewlett-Packard 4280A C meter at 1 MHz. The elastic modulus was measured using nanoindentation (Shimadzu DUH W201S) with a 3-sided diamond indenter, a 4-cycle loading/unloading routine and loads of 0.1-2.0 mN.

With the work presented herein the inventors have demonstrated for the first time that a molecule with more than one organic bridging group bound to each Si atom by a Si—C bond can be fashioned into a periodic mesoporous organosilica to create a new class of materials that we call high organic group content periodic mesoporous organosilicas (HO-PMO's).

The high organic group content of the described examples was achieved by the use of $[SiR]_3$ ring building blocks of the material. It will therefore be appreciated that other materials comprised of rings with other ring sizes, condensed rings (cages), and interlinked rings with different organic groups can also be produced according to the present invention to give HO-PMOs.

The invention presented represents the first examples of porous polymeric materials with pores >0.3 nm comprised of $[ER]_n$ (n>1) building units (E is for the described examples Si) with E-C bonds and E interconnected by other atoms E. It therefore will be appreciated that other inorganic elements E instead of Si can be used in such a ring building unit $[ER]_n$ n>1, for example, but not restricted to E=Si, Ge, Sn, P, B, Ti, and Zr. Furthermore it can be expected that the ring building units $[ER]_n$ can also be interconnected by other inorganic elements but O, for example, but not restricted to N, S, P, B.

The pore sizes may tuned over a wide range from 0.3 nm (for example when a small molecule or short chain surfactant is used as template) to 1000 nm (for example when a colloidal crystal template is used). It will be known to those skilled in the art that the pore size distribution can vary from very narrow to very broad depending on the reaction conditions. It can be furthermore expected that also non-porous materials with $[ER]_n$ building units can be made using sol-gel type reaction for polycondensing the precursor molecule without a template.

This variability makes the material important and useful for a broad range of applications. Non-limiting examples of applications are low-k materials for microelectronics, separation technologies, e.g. chiral drug separations or waste water cleaning, catalysis, biodelivery, chemical storage, e.g. gas storage, and sensors including biosensors.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. D. J. Brondani, R. J. P. Corriu, S. El Ayoubi, J. E. Moreau, M. W. C. Man, *Tetrahedron Letters* 34, 2111 (1993).
2. L. Dome, N. Alikacem, R. Guidoin, M. Auger, *Magn. Reson. Med.* 34, 548 (1995).
3. V. M. Litvinov, H. Barthel, J. Weis, *Macromolecules,* 35, 4356 (2002).
4. T. Asefa, M. J. MacLachlan, N. Coombs, G. A. Ozin, *Nature* 402, 867 (1999).
5. S. Inagaki, S. Guan, Y. Fukushima, T. Ohsuna, O. Terasaki, *J. Am. Chem. Soc.* 121, 9611 (1999).
6. B. J. Melde, B. T. Holland, C. F. Blanford, A. Stein, *Chem. Mater.* 11, 3302(1999).
7. T. Asefa, M. J. MacLachlan, H. Grondey, N. Coombs, G. A. Ozin, *Angew. Chem. Int Ed.* 39, 1808 (2000).

Therefore what is claimed is:

1. A periodic porous material comprised of $[SiR]_n$ rings, wherein SiR units within a ring are interconnected by Si—R bonds, each Si atom being bound to two or more organic groups which bridge said Si atoms, and wherein said $[SiR]_n$ rings are interconnected by oxygen atoms O via Si—O bonds, in which R is an organic group, n is an integer >1, said material having periodic pores, said pores have a diameter in a range from about 0.5 nm to about 1000 nm.

2. The material according to claim 1 wherein the n organic groups R in the $[SiR]_n$ ring are either all identical, all different from each other, or some of them are identical and the remaining ones are different.

3. The material according to claim 1 wherein at least two $[SiR]_n$ rings share at least one Si—C bond.

4. The material according to claim 1 wherein a discrete number of $[SiR]_n$ rings are interconnected by an organic group linking the organic groups of the discrete number of $[SiR]_n$ rings.

5. The material according to claim 1 formed as a powder.

6. The material according to claim 1 formed as a film.

7. The material according to claim 1 formed as a monolith.

8. The material according to claim 6, exhibiting a dielectric constant (k) in a range from about 2.0 to about 3.6.

9. The material according to claim 6, which exhibits optical transparency for visible light.

10. The material according to claim 6, which exhibits an elastic modulus in a range from about 8.7 GPa to about 11.8 GPa.

11. The material according to claim 6, which is hydrophobic.

12. The material according to claim 1 wherein each of the $[SiR]_n$ rings has n equal to the same integer.

13. The material according to claim 1 wherein the material is made up of a mixture of $[SiR]_n$ rings with non-identical n values.

14. The material according to claim 1 including additional terminal organic groups bound to some, but not necessarily all Si atoms.

15. The material according to claim 1 including acyclic units comprising $SiO_4$, or $SiO_3R$ wherein the $[SiR]_n$ rings and the acyclic units are interconnected by the O atoms.

16. The material according to claim 1 produced by a method comprising the steps of;

polycondensing a cyclic molecule containing said $[SiR]_n$ rings under conditions suitable for polycondensation of the cyclic molecule in the presence of a template material under conditions suitable for self-assembly of the cyclic molecule and removing the template material from the self-assembled cyclic molecule.

17. The material according to claim 16 wherein said cyclic molecule containing said $[SiR]_n$ rings are selected from the group consisting of compounds 1 $[SiCH_2(OEt)_2]_3$, 2 $[SiCH_2(OEt)_2]_2[SiCHBr(OEt)_2]$, 3 $[SiCH_2(OEt)_2]_2[SiCHI(OEt)_2]$, 4 $[SiCH_2(OEt)_2]_2[SiCHEt(OEt)_2]$, 5 $\{[(EtO)_2SiCH_2]_2[(EtO)_2SiCH]\}_2\{(CH_2)_3\}$ and 6 $\{[(EtO)_2SiCH_2]_2[(EtO)_2SiCH]\}_2\{CH_2CHCHCH_2\}$.

18. The material produced according to the method of claim 16 wherein the template material is selected from the group consisting of non-ionic surfactants, ionic surfactants, colloidal crystals, polymers, hyper branched molecules, star-shaped molecules, macromolecules, dendrimers, and combinations thereof.

19. The material produced according to the method of claim 16 including a step of heating the material to a temperature greater than about 100° C. to induce a "self-hydrophobization".

20. The material produced according to the method of claim 16 wherein a size of the pores is selected by choosing the template material having suitable dimensions so that when it is removed pores of selected size are formed.

* * * * *